US008715641B2

(12) United States Patent
Filutowicz et al.

(10) Patent No.: US 8,715,641 B2
(45) Date of Patent: *May 6, 2014

(54) THERAPEUTIC AMOEBA AND USES THEREOF

(71) Applicant: Amebagone, LLC, Madison, WI (US)

(72) Inventors: Marcin Filutowicz, Madison, WI (US); Katarzyna Dorota Borys, Stoughton, WI (US)

(73) Assignee: Amebagone, LLC, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/040,107

(22) Filed: Sep. 27, 2013

(65) Prior Publication Data
US 2014/0030227 A1 Jan. 30, 2014

Related U.S. Application Data

(63) Continuation of application No. 13/152,993, filed on Jun. 3, 2011, now Pat. No. 8,551,471.

(60) Provisional application No. 61/396,774, filed on Jun. 3, 2010.

(51) Int. Cl.
*A01N 63/00* (2006.01)

(52) U.S. Cl.
USPC .......................................... 424/93.1

(58) Field of Classification Search
None
See application file for complete search history.

(56) References Cited

U.S. PATENT DOCUMENTS

| 5,051,365 A | 9/1991 | Polne-Fuller |
| 5,518,919 A | 5/1996 | Tyndall |
| 2009/0162393 A1 | 6/2009 | Cook |

OTHER PUBLICATIONS

A Duczek, LJ A Wildermuth, "Populations of amoebae which feed on conidia and hyphae of *Bipolaris sorokiniana* in Queensland soils" J Australasian Plant Pathology 1991,20:81-85.
Barclay SL & Meller E, "Efficient transformation of *Dictyostelium discoideum* amoebae." Mol Cell Biol. 1983, 3 (12):2117-30.
Bassetti M, et al. 2008. "Drug treatment for multidrug-resistant *Acinetobacter baumannii* infections." Fut. Microbiol. 2000, 3(6):649-60.
Williams KL et al. "Genetics of growth in axenic medium of the cellular slime mould *Dictyostelium discoideum*." Nature 1974, 247:142-143.
Bielecki J, et al. "*Bacillus subtilis* expressing a haemolysin gene from *Listeria monocytogenes* can grow in mammalian cells." Nature 1990, 345:175-176.
Brefeld O. "Dictyostelium mucorides. Ein Neurer Organismus aus der Verwandtschaft der Myxomyceten." Abh. Seckenberg Naturforsch. Ges. 7 1869: 85-107.

Cavender JC, Raper KB. "The Acrasieae in Nature. I. Isolation." Am J Bot 1965, 52: 294-6.
Chakraborty, et al., "The Reduction of Root Colonization by Mycorrhizal Fungi by mycophagous amoebae." Canadian J. of Microb. 1985, 31:295-297.
Chambers HF & Hegde SS. "Combating the growing problem of methicillin-resistant *Staphylococcus aureus*: do the newer antibiotics represent a better alternative to vancomycin?"Expert Rev Anti Infect Ther. 2007, 5(3):333-5.
Chen G, et al. "Immune-like phagocyte activity in the social amoeba." Science 2007, 317(5838):678-8.
Cohen ML. "Changing patterns of infectious disease." Nature 2000, 406:762-767.
Cursons et al., "Immunity to pathogenic free-living amoebae: role of humoral antibody." Infect Immun 1980, 29(2): 401-7.
D'Costa et al. "Sampling the antibiotic resistome." Science 2006, 311(5759):374-7.
Eichinger L. et al. 2005. "The genome of the social amoeba *Dictyostelium discoideum*." Nature 2005, 435(7038):43-57.
Ferrante A. "Free-living amoebae: pathogenicity and immunity." Parasite Immunol 13(1): 31-47, Jan. 1991.
Frazee BW, et al. "High prevalence of methicillin-resistant *Staphylococcus aureus* in emergency department skin and soft tissue infections." Ann Emerg Med. 2005, 45(3):311-20.
Garazzino S, et al. "Haematological safety of long-term therapy with linezolid." 2007 Int J Antimicrob Agents. 29:480-483.
Garrabou G, et al. "Reversible inhibition of mitochondrial protein synthesis during linezolid-related hyperlactatemia." 2007. Antimicrob Agents Chemother. 51(3):962-967.
Johnson, K.B., and Stockwell, V.O. 2000. Biological control of fire blight. pp. 319-337 in: Fire Blight—the Disease and its Causative Agent, Erwinia amylovora, J.L. Vanneste, ed. CAB International, New York.
Kaka AS, et al. "Bactericidal activity of orally available agents against methicillin-resistant *Staphylococcus aureus*." J. Antimicrob Chemother. 2006, 58(3):680-683.
Lawrence KR, et al. "Serotonin toxicity associated with the use of linezolid: a review of postmarketing data." Clin Infect Dis. 2006, 42(11):1578-83.
Liwerant IJ & Pereira da Silva LH. "Comparative mutagenic effects of ethyl methane-sulfonate, n-methyl-n'-nitro-n-nitrosoguanidine, ultraviolet radiation and caffeine on *Dictyostelium discoideum*." Mutat Res. 1975, 33(2-3):135-46.
Loomis, WF Jr. 1971. "Sensitivity of *Dictyostelium discoideum* to nucleic acid analogues." Exp Cell Res. 1970, 64:484-486.
Mahgoub S. et al. "Completely resistant *Acinetobacter baumannii* strains." Infect Control Hosp Epidemiol. 2002, 23 (8):477-9.
Maragakis LL & Perl TM. "*Acinetobacter baumannii*: epidemiology, antimicrobial resistance, and treatment options." Clin Infect Dis. 2008, 46:1254-1263.
Mazel D & Davies J., "Antibiotic resistance in microbes." Cell Mol Life Sci. 1999. 56(9-10):742-54.
McDougal, et al., "Pulsed-field gel electrophoresis typing of oxacillin-resistant *Staphylococcus aureus* isolates from the United States: establishing a national database." J Clin Microbiol. 2003, 41(11):5113-20.

(Continued)

*Primary Examiner* — Suzanne M Noakes
*Assistant Examiner* — Stephen Chong
(74) *Attorney, Agent, or Firm* — Tanya A. Arenson; Casimir Jones, S.C.

(57) ABSTRACT

The present invention relates to amoebae (slime molds) and uses thereof. In particular, the present invention relates to the use of amoebae or their environmentally stable spores to treat microbial infections and other uses.

22 Claims, 44 Drawing Sheets

(56) References Cited

OTHER PUBLICATIONS

North MJ & Williams KL., "Relationship Between the Axenic Phenotype and Sensitivity to w-Aminocaboxylic Acids in *Dictyostelium discoideum*." J. Gen. Microbiol. 1978, 107:223-230.

Old, K. M. et al., "Fine structure of a new mycophagous amoeba and its feeding on *Cochliobolus sativus*." Soil Biology and Biochemistry 1985, 17(5):645-655.

Prins JM, et al. "Clinical relevance of antibiotic-induced endotoxin release." Antimicrob Agent Chemother. 1994, 38 (6):1211-1218.

Proctor RA. "Role of folate antagonists in the treatment of methicillin-resistant *Staphylococcus aureus* infection." Clin Infect Dis. 2008, 46(4):584-593.

Raper & Smith, "The Growth of *Dictyostelium discoideum* upon Pathogenic Bacteria." J Bacteriol. 1939, 38(4): 431-45.

Raper KB. "Factors Affecting Growth and Differentiation in Simple Slime Molds." Mycologia 1956, 48(2):160-205.

Raper KB. "Isolation, cultivation, and conservation of simple slime molds." Q Rev Biol 1951, 26(2): 169-90.

Raper, K. B., and C. Thorn, "Interspecific Mixtures in the Dictyosteliaseae." Am. J Botany 1941, 28:69-78.

Rodríguez S, Bishop P. "Three-dimensional quantification of soil biofilms using image analysis." Environ Eng Sci 24: 96-103, Jan. 2007.

Schaap, et al."Molecular Phylogeny and Evolution of Morphology in the Social Amoebas" 2006 Science, 314 (5799):661-3.

Singh BN. "Studies on soil Acrasieae; distribution of species of *Dictyostelium* in soils of Great Britain and the effect of bacteria on their development." J Gen Microbiol (1947), 1(1): 11-21.

Smith MG, et al. "New insights into *Acinetobacter baumannii* pathogenesis revealed by high-density pyrosequencing and transposon mutagenesis." Genes Dev. 2007, 21(5):601-14.

Sternfeld et al., "Cell differentiation in *Dictyostelium* under submerged conditions." Proc Natl Acad Sci 1977, 74(1): 268-71.

Sucgang et al., "Comparative genomics of the social amoebae *Dictyostelium discoideum* and *Dictyostelium purpureum*." Genome Biology 2011, 12(2):R20.

Sussman M, 1966. Biochemical and genetic methods in the study of cellular slime mold development. pp. 397-410. In: Methods in Cell Physiology, vol. 2, Edited by D Prescott. Academic. Press, New York.

Sussman R & Sussman M. "Cultivation of *Dictyostelium discoideum* in axenic medium." Biochem. Biophys. Res. Commun. 1967, 29(1):53-5.

Swanson A, Vadell E, Cavender J. (2001) Global distribution of forest soil *dictyostelids* J Biogeo 26(1): 133-48.

Schuster et al., "Free-living amoebae as opportunistic and non-opportunistic pathogens of humans and animals." Intl Journal for Parsitology 2004, 34: 1001-1027.

Evsigneeva et al., "Amoeba co-culture of soil specimens recovered 33 different bacteria, including four new species and *Streptococcus pneumoniae*." Microbiology 2009, 155:657-664.

Molmeret et al., "Amoebae as training Grounds for Intracellular Bacterial Pathogens." Applied and Environmental Microbiology Jan. 2005, p. 20-28.

| Temp. STRAIN | Sporulation (hrs of incubation) | | | Clearing (zone in mm) | | |
|---|---|---|---|---|---|---|
| | RT | 30° C | 37° C | RT | 30° C | 37° C |
| Salvador | 24 hr | 24 hr | 24 hr | 5 mm | 10 mm | 10 mm |

| Temp. STRAIN | Sporulation | | Clearing | |
|---|---|---|---|---|
| | RT | 30° C | RT | 30° C |
| WS 371A | 48 hr | 48 hr | 18 mm | 22 mm |
| WS321.5 | 24 hr | 24 hr | 24 mm | 33 mm |
| WS321.7 | 24 hr | 24 hr | 11 mm | 21 mm |
| Tu-4b | 48 hr | | 3 mm | |
| X3 | 24 hr | | 10 mm | 2 mm |
| Turkey 27 | 24 hr | | 20 mm | |
| WS 309 | 72 hr | 48 hr | 10 mm | 7 mm |
| WS 57-7 | 24 hr | | 30 mm | |
| FR14 | 48 hr | | 26 mm | 2 mm |
| WI647 | 24 hr | | 25 mm | 2 mm |
| WS142 | 24 hr | 24 hr | 30 mm | 35 mm |
| WS255x28 | 24 hr | 48 hr | 30 mm | |

Key:
- 24 hr of incubation
- 48 hr of incubation
- 72 hr of incubation
- No Growth
- 0-9mm zone
- 10-20mm zone
- 21-40mm zone

| Amoebae | Presence of serum |
| --- | --- |
| | Non-nutrient soft agar |
| WS 647 |  |
| WS 142 |  |
| Salvador |  |
| Turkey 27 |  |

| WS 57.7 |  |
|---|---|
| WS 321.5 |  |
| WS 321.7 | NOT DETERMINED |
| WS 371A |  |
| X3 |  |

| | Klebsiella pneumoniae | |
|---|---|---|
| Amoebae | COLUMN A | COLUMN B |
| | Presence of serum | Absence of serum |
| | Non-nutrient soft agar | Non-nutrient soft agar |
| WS 647 |  |  |
| WS 142 | NOT DETERMINED |  |
| Salvador |  |  |

| Amoebae | COLUMN A | COLUMN B |
|---|---|---|
| Turkey 27 |  |  |
| WS 57.7 |  |  |
| WS 321.5 |  |  |

| AMOEBAE | COLUMN A | COLUMN B |
|---|---|---|
| WS 321.7 |  | NOT DETERMINED |
| WS 371A |  |  |
| X3 |  |  |

| AMOEBAE | COLUMN A | COLUMN B |
|---------|----------|----------|
| FR 14 |  | |

Figure 13

| Amoebae | Wide Type Staphylococcus K+ | | | |
|---|---|---|---|---|
| | COLUMN A | | COLUMN B | |
| | Absence of serum | | Presence of serum | |
| | Non-nutrient soft agar | SM2 soft agar | Non-nutrient soft agar | SM2 soft agar |
| WS 647 | | | | NOT DETERMINED |
| WS 142 | | | | NOT DETERMINED |
| Salvador | | | | NOT DETERMINED |

| Amoebae | COLUMN A | | COLUMN B | |
|---|---|---|---|---|
| Turkey 27 |  |  |  | NOT DETERMINED |
| WS 57.7 |  |  |  | NOT DETERMINED |
| WS 321.5 |  |  | | NOT DETERMINED |

| AMOEBAE | COLUMN A | | COLUMN B | |
|---|---|---|---|---|
| WS 321.7 | | | NOT DETERMINED | NOT DETERMINED |
| WS 371A | | | | NOT DETERMINED |
| X3 | | | NOT DETERMINED | |
| WS 309 | | | | NOT DETERMINED |

| AMOEBAE | COLUMN A | COLUMN B |
|---|---|---|
| WS 309 |  |  |
| WS 255X281 |  |  |

THERAPEUTIC AMOEBA AND USES THEREOF

This application is a continuation of U.S. application Ser. No. 13/152,993 filed Jun. 3, 2011, which claims priority to U.S. provisional application Ser. No. 61/396,774, filed Jun. 3, 2010, each of which are herein incorporated by reference in its entirety.

FIELD OF THE INVENTION

The present invention relates to amoebae (slime molds) and uses thereof. In particular, the present invention relates to the use of amoebae or their environmentally stable spores to treat microbial infections and other uses.

BACKGROUND OF THE INVENTION

Bacterial pathogens are becoming increasingly resistant to multiple antibiotics, rendering what were once considered miracle cures ineffective (Cohen M L. 2000. Nature. 406: 762-767). Without these medicines, clinicians must resort to alternative drugs. Often these drugs are less effective than their predecessors, and they have more side effects. Worse, in some instances, alternative drugs are not an option. Pathogens have been isolated that are resistant to all of the Federal Drug Administration's (FDA) approved antibiotics (Mahgoub S, et al. 2002. Infect Control Hosp Epidemiol. 23:477-479). These organisms are intractable pathogens, the harbingers of civilization's return to a pre-antibiotic era and the suffering this era would entail.

Both in its depth and breath, the problem of antibiotic resistance in pathogens is growing. These pathogens quickly arise and spread. To a large degree, this phenomenon is the result of the rapid acquisition and dissemination of genes that confer antibiotic resistance (D'Costa V M, et al. 2006. Science. 311:374-377; Walsh C 2003. Antibiotics: Actions, Origins, Resistance, ASM Press, Washington, D.C.). Bacteria, even of different genera, can share resistance elements through the processes of transformation, transduction, and conjugation (Mazel D & Davies J. 1999. Cell Mol Life Sci. 56:742-754). As a direct consequence of this transfer, antibiotic resistance genes in the environment have become ubiquitous, and pan-antibiotic-resistant pathogens have emerged. Without swift and creative action by the research and development community, infection may once again become the leading cause of suffering and death in the world.

Present day examples of superbugs are MRSA (methicillin resistant *Staphylococcus aureus*) (McDougal, et al., 2003. J. of Clin. Microb., November, p. 5113-5120 Vol. 41, No. 11) and MDR (multi-drug resistant) *Acinetobacter baumannii*. Collectively, these organisms are responsible for over forty-percent of all nosocomial infections and over fifty-percent of dermatological infections that require hospitalization (Bassetti M, et al. 2009. Fut. Microbiol. 3:649-660; Frazee B W, et al. 2005. Ann Emerg Med. 45:311-320). All the current oral treatment options for MRSA have drawbacks (Chambers H F & Hegde S S. 2007. Expert Rev Anti Infect Ther. 5:333-335). Linezolid is very expensive, counter indicated for long term therapy, and has notable toxicities including myelotoxicity, lactic acidosis, serotonin syndrome, and peripheral neuropathy (Garazzino S, et al. 2007. Int J Antimicrob Agents. 29:480-483; Garrabou G, et al. 2007. Antimicrob Agents Chemother. 51:962-967; Lawrence K R, et al. 2006. Clin Infect Dis. 42:1578-1583). MRSA are becoming increasingly resistant to tetracyclines, fluoroquinolones, clindamycin, and vancomycin, and these antibiotics are rapidly becoming non-effective treatments (Kaka A S, et al. 2006. J Antimicrob Chemother. 58:680-683). Furthermore, sulfamethoxazole-trimethoprim has recently been shown to have a treatment failure rate of fifty-percent (Proctor R A. 2008. Clin Infect Dis. 46:584-593).

The situation for MDR *A. baumannii* is also troubling. MDR strains of this organism have been isolated that are resistant to all approved frontline and secondary antibiotics (Maragakis L L & Perl T M. 2008. Clin Infect Dis. 46:1254-1263). Without effective treatments, patients with MRSA or MDR *A. baumannii* infections have longer periods of hospitalization, increased morbidity, and a greater likelihood of in-hospital death (Bassetti M, et al. 2009. Fut Microbiol. 3:649-660; Frazee B W, et al. 2005. Ann Emerg Med. 45:311-320).

Antibiotic resistance problem is not limited in its scope to medical settings. Antibiotic uses and misuses in veterinary science and in agriculture are a global and rapidly growing issue. For example, "fire blight, caused by *Erwinia amylovora*, is a major threat to apple and pear production worldwide. Nearly all pear varieties and many of the most profitable apple varieties and horticulturally-desirable rootstocks planted throughout the U.S. are highly susceptible to fire blight. Therefore, most growers apply the antibiotics streptomycin or oxytetracycline one to three times during bloom to prevent growth of *E. amylovora*. Although streptomycin and oxytetracycline are effective in preventing fire blight on blossoms, their application likely drives antibiotic resistance in the environment and in the food chain. Innovative approaches are desperately needed to reign in fire blight, a disease that has been smoldering in orchards for more than a century and raging out of control over the past decade. An additional societal benefit of non-conventional treatments of fire blight is the elimination of the bulk of antibiotic use in plant agriculture, since greater than 90% of antibiotics applied to plants is for the control of that disease (Johnson, K. B., and Stockwell, V. O. 2000. Biological control of fire blight. Pages 319-337 in: Fire Blight—the Disease and its Causative Agent, *Erwinia amylovora*, J. L. Vanneste, ed. CAB International, New York).

What is needed are new treatments for microbial infections in animals, plants and environmental settings.

SUMMARY OF THE INVENTION

The present invention relates to amoebae (slime molds) and uses thereof. In particular, the present invention relates to the use of amoebae or their environmentally stable spores to treat microbial infections and other uses.

For example, in some embodiments, the present invention provides a method of killing or slowing the rate of growth of a microorganism (e.g., treating a microbial infection), comprising: contacting a microorganism with a composition (e.g., a pharmaceutical composition) comprising one or more species of amoebae, wherein the contacting kills or slows the growth of the microorganism. In some embodiments, the microorganism is a bacteria (e.g., a pathogenic bacteria such as MRSA, multi-drug resistant bacteria or persister cells of a bacteria) or a fungus. In some embodiments, the microorganisms are present in planctonic or biofilm forms. In some embodiments, the microorganism is in or on a subject. For example, in some embodiments, the microorganism is present in a wound, a mucus membrane (e.g., nostril, throat, rectum, vagina, etc.), a tissue or an organ of the subject. In some embodiments, the wound is at a temperature above the normal body temperature of the subject or is hypoxic. In some embodiments, the microorganism is in or on a plant (e.g., an agricultural or industrial plant). In some embodiment, the composition comprises two or more species of amoebae. The present invention is not limited to a particular strain or species of amoebae. Examples include, but are not limited to, *Polyspondillum palidum* Salvador, ibid WS 371A, *D. discoideum* WS 647, *Dictyostelium giganteum* WS 142, Turkey 27, *Actyostilium leptosomum* WS 57.6, *Dictyostelium purpureum* WS 321.5, ibid WS 321.7, *Dictyostelium discoideum* X3, WS309, WS 255×281 (hybrid of unknown species), *Dictyostelium lavandullum* Tu4b or *Polispondillum candidum* FR14. In some embodiments, the composition further comprises a non-amoebae anti-microbial agent, along with one or more carriers or other components.

Certain embodiments of the invention provide a method of treating a subject (e.g., a human) infected with a microorganism, comprising: contacting a subject infected with a microorganism with a pharmaceutical composition comprising one or more species of amoebae, wherein the contacting kill the microorganism.

Additional embodiments provide kits, compositions (e.g., pharmaceutical compositions), comprising: one or more species of amoebae; and a carrier (e.g., a pharmaceutically acceptable carrier).

In some embodiments, the present invention provides for the use of a pharmaceutical composition comprising a) one or more species of amoebae; and b) a pharmaceutically acceptable carrier in the treatment of a subject infected with a microorganism.

DESCRIPTION OF THE FIGURES

FIG. 9 shows growth of amoebae at temperatures encountered in skin wounds.

DEFINITIONS

Figure 1:
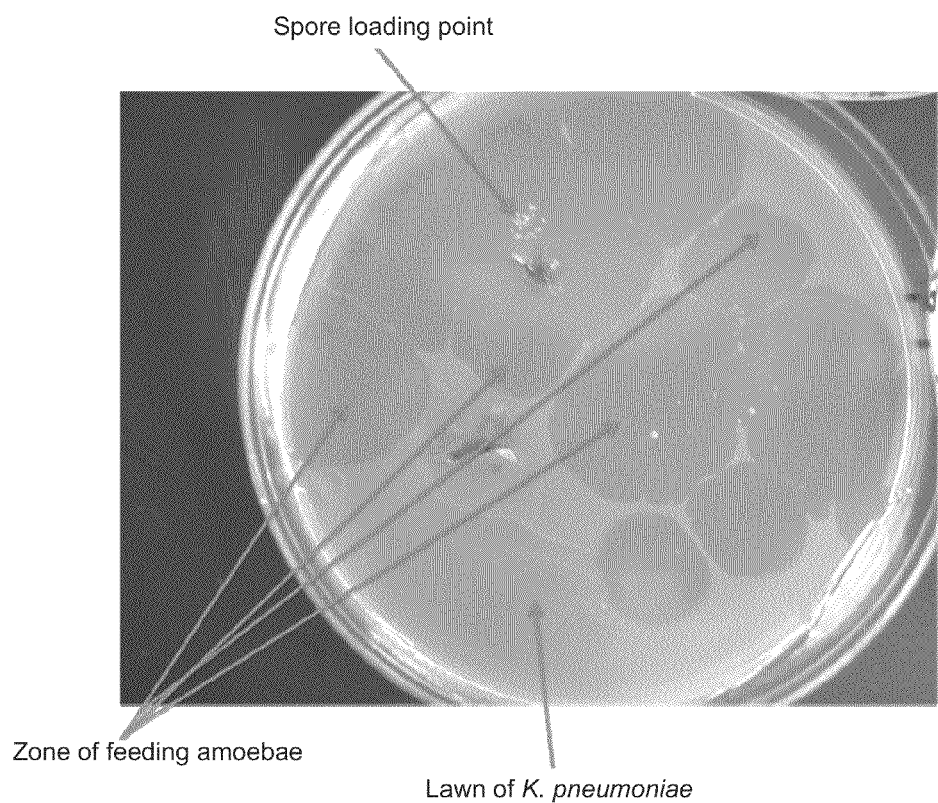
FIG. 1 shows a photograph of feeding amoebae.

To facilitate an understanding of the present invention, a number of terms and phrases are defined below.

The term "medical devices" includes any material or device that is used on, in, or through a subject's or patient's body, for example, in the course of medical treatment (e.g., for a disease or injury). Medical devices include, but are not limited to, such items as medical implants, wound care devices, drug delivery devices, birth control and body cavity and personal protection devices. Examples of medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incision drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, intrauterine devices (IUDs), diaphragms, and condoms.

The term "therapeutic agent," as used herein, refers to compositions (e.g., comprising amoebae) that decrease the infectivity, morbidity, or onset of mortality in a subject contacted by a pathogenic microorganism or that prevent infectivity, morbidity, or onset of mortality in a host contacted by a pathogenic microorganism. As used herein, therapeutic agents encompass agents used prophylactically, e.g., in the absence of a pathogen, in view of possible future exposure to a pathogen. Such agents may additionally comprise pharmaceutically acceptable compounds (e.g., adjutants, excipients, stabilizers, diluents, and the like). In some embodiments, the therapeutic agents of the present invention are administered in the form of topical compositions, injectable compositions, ingestible compositions, and the like. When the route is topical, the form may be, for example, a solution, cream, ointment, salve or spray.

As used herein, the term "pathogen" refers to a biological agent that causes a disease state (e.g., infection, cancer, etc.) in a host. "Pathogens" include, but are not limited to, bacteria, fungi, archaea, protozoans, mycoplasma, and other parasitic organisms.

As used herein, the term "microorganism" refers to any species or type of microorganism, including but not limited to, bacteria, archea, fungi, protozoans, mycoplasma, and parasitic organisms. The present invention contemplates that a number of microorganisms encompassed therein will also be pathogenic to a subject.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process that is well known in the art. (See e.g., Finegold and Martin, Diagnostic Microbiology, 6th Ed., CV Mosby St. Louis, pp. 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red. In some embodiments, the bacteria are those capable of causing disease (pathogens) and those that cause production of a toxic product, tissue degradation or spoilage.

As used herein, the term "fungi" is used in reference to eukaryotic organisms such as the molds and yeasts, including dimorphic fungi.

As used herein, the term "non-human animals" refers to all non-human animals including, but are not limited to, vertebrates such as rodents, non-human primates, ovines, bovines, lagomorphs, porcines, caprines, equines, canines, felines, ayes, etc.

As used herein the term "biofilm" refers to an aggregation of microorganisms (e.g., bacteria) surrounded by an extracellular matrix or slime adherent on a surface in vivo or ex vivo, wherein the microorganisms adopt altered metabolic states.

As used herein, the term "subject" refers to organisms to be treated by the methods of embodiments of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a amoebae of the present invention and optionally one or more other agents) for a condition characterized by infection by a microorganism or risk of infection by a microorganism.

The term "diagnosed," as used herein, refers to the recognition of a disease by its signs and symptoms (e.g., resistance to conventional therapies), or genetic analysis, pathological analysis, histological analysis, diagnostic assay (e.g., for microorganism infection) and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "genome" refers to the genetic material (e.g., chromosomes) of an organism or a host cell.

As used herein, the term "effective amount" refers to the amount of a therapeutic agent (e.g., an amoebae) sufficient to effect beneficial or desired results. An effective amount can be administered in one or more administrations, applications or dosages and is not intended to be limited to a particular formulation or administration route.

As used herein, the term "co-administration" refers to the administration of at least two agent(s) (e.g., an amoeba) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

The term "sample" as used herein is used in its broadest sense. A sample may comprise a cell, tissue, or fluids, nucleic acids or polypeptides isolated from a cell (e.g., a microorganism), and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "modulate" refers to the activity of a compound (e.g., an amoebae) to affect (e.g., to kill or prevent the growth of) a microorganism.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., infection by a microorganism). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that treat or prevent infection by a microorganism.

DETAILED DESCRIPTION OF THE INVENTION

The present invention relates to amoebae (slime molds) and uses thereof. In particular, the present invention relates to the use of amoebae or their environmentally stable spores to treat microbial infections and other uses.

Embodiments of the present invention provide for the use of amoebae (slime molds) in treatment and prevention of microbial infection, in particular, against some of the most tenacious pathogens. Over millions of years amoebae have evolved to safely kill a broad range of pathogenic bacteria. They eat pathogens while leaving no toxic debris, they can be applied to wounds, and they do not harm patients. In many ways, amoebae are the microscopic cousins of maggots, which themselves received FDA approval to be marketed for medical use. The benefits of "bio-surgery" are established and include the potential to be used in combination with chemical antibiotics. Combinatorial therapies can reduce the risk of pathogens acquiring and spreading antibiotic resistance. Amoebae offer many of the same advantages as maggots, while their microscopic, spore-forming lifestyle and the parallels to be drawn with phagocytic immune cells make them more appealing, less expensive to make, and more convenient to use. The utility of amoebic therapy derives from amoebae (or their spores) being an easily transported and applied antibacterial agent, effective against a broad range of pathogens including drug resistant bacteria.

In human medicine, the use of amoebae feeding on bacteria finds use for application at non-sterile sites (e.g. the skin or mucosal surfaces). At these sites, overwhelming numbers of amoebae are used to quickly consume pathogenic bacteria. Since amoebae possess the ability to consume wound bacteria, especially pathogens that are impervious to chemical antibiotics, they further find use as an effective prophylactic, an adjunct to current therapies, or an independent remedy. In some embodiments, amoebae (or their germinating spores) are applied to infected tissue where they quickly reduce the microbial load and, in doing so, promote healing. The patient populations that benefit from this form of therapy are those with, for example, diabetic skin lesions, burns, and surgical or chance wounds. Amoebae further find use in a variety of additional applications. Examples include, but are not limited to, veterinary science, agriculture, food industry and industrial settings (e.g., prevention or remediation of fouling of machine parts, water lines, medical devices, etc.).

Figure 2:
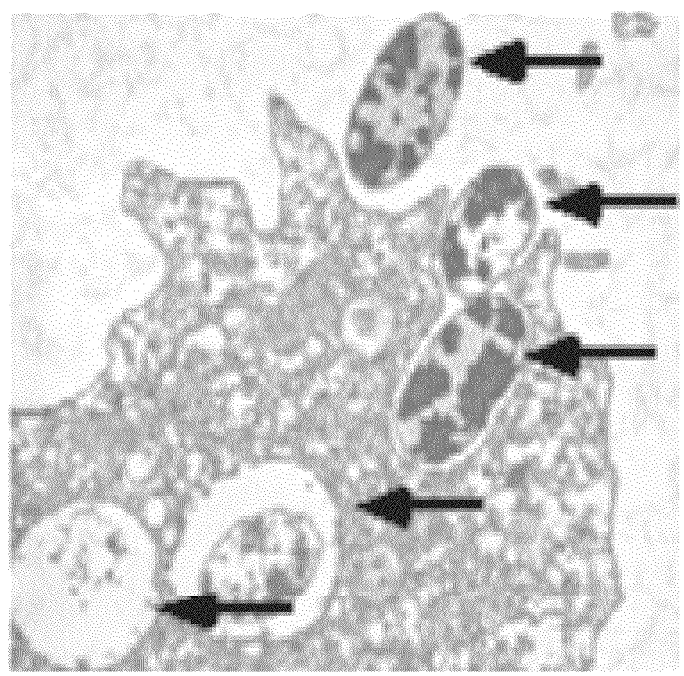
FIG. 2 shows an electron micrograph showing several stages of amoebic phagocytosis. (Clockwise from the top): Free *Klebsiella aerogenes; D. discoideum* forms a cup structure and begins to engulf the bacteria. The bacteria, sequestered within a phagosome are digested (image reproduce from Cohen M L. 2000. Nature. 406: 762-767).
Figure 3:
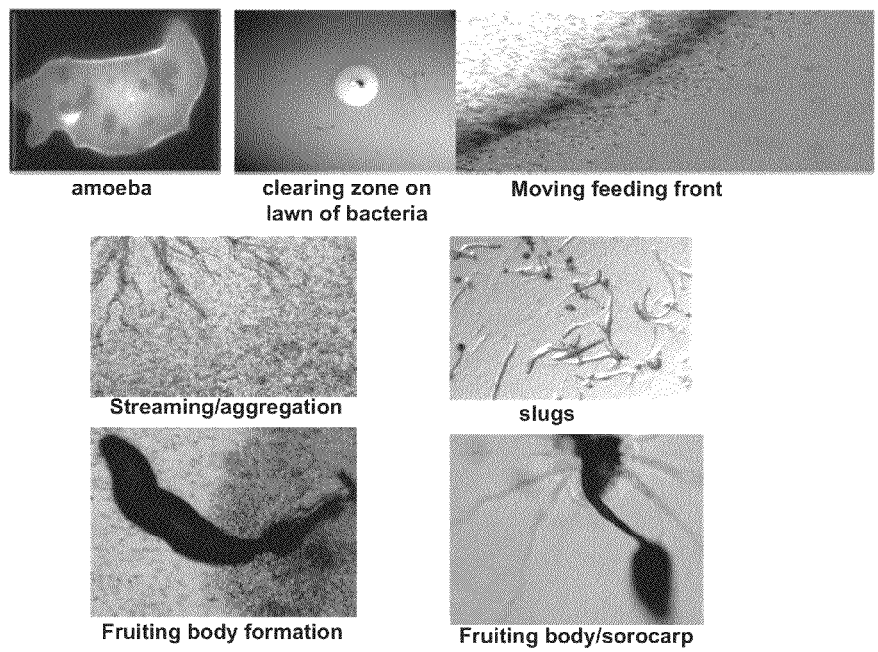
FIG. 3 shows a) development stages of soil-borne amoeba and b) lifecycle of *D. discoideum* (Modified from Science 325:1199). The social amoebae belonging to the phylum Mycetozoa have been described as primitive eukaryotes that exhibit characteristics found among both protozoans and fungi (Bonner J T. (2009) The social amoebae: the biology of cellular slime molds; Raper et al., (1984) The Dictyostelids). This description can be summarized in an illustration of their asexual life cycle. Each species of amoeba has a vegetative phase where, as microscopic unicellular protists, independent amoeboid cells feed upon bacteria, grow, and multiply. When the amoebae exhaust their bacterial food source, they enter a social phase in which individual cells stream together to form a multicellular, differentiated, mobile slug. Since growth occurred at the single-cell stage, its size depends on how many amoebae have entered the aggregate, and slugs will vary in length from about 0.2 to 2 millimeters, a ten fold range, and by the latest estimates the number of amoebae they contain ranges from about 10,000 to 2 million. The slug eventually comes to rest and develops into a macroscopic fruiting body consisting of a stalk with sorocarp. Within the sorocarp are environmentally and temporally stable spores, which are disseminated by the wind, animals, or the forces generated by the sorocarp falling. From each viable spore a single amoeba arises.
Figure 3:
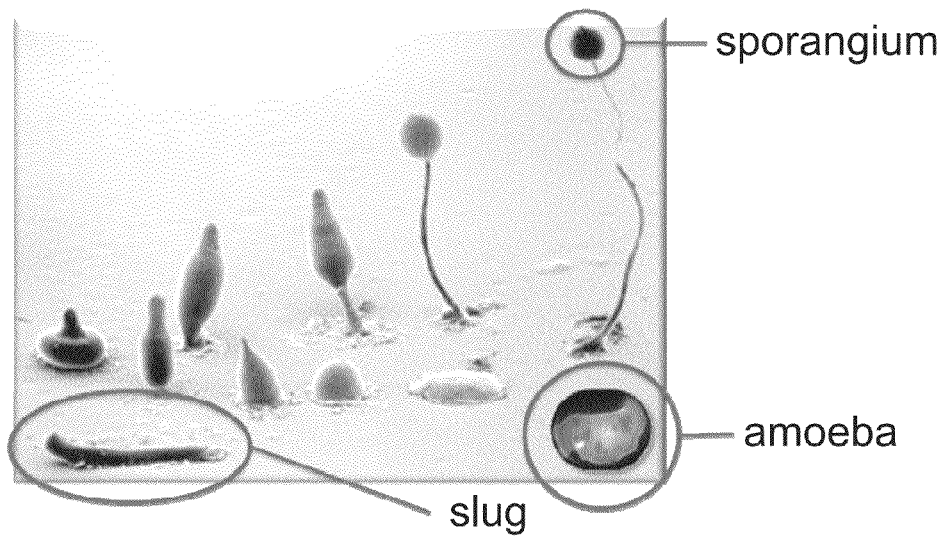

The ability of slime molds to feed on bacteria and fungi is described (Raper K B. 1984. The Dictyostelids. Princeton University Press. Princeton N.J.; Old, K. M. et al., .1985 Fine structure of a new mycophagous amoeba and its feeding on *Cochliobolus sativus*; S. Chakraborty, et al., 1985, Canadian J. of Microb, 31:295-297; Soil Biology and Biochemistry Vol 17, 645-655; A Duczek, U % A Wildermuth, G B 1991 J Australasian Plant Pathology Vol 20, 81-85). Experiments conducted during the course of developments of embodiments of the present invention demonstrated killing of bacteria spread on a surface of agar plate (FIG. 1). When a few spores are added, in a matter of hours they split open and from each spore emerges a single amoeba that immediately begins to feed on the surrounding bacteria. As they grow they divide in two (e.g., approximately every three hours) so vast numbers of amoebae are soon present. The soil-born amoebae feed first as independent soil amoebae. Each individual amoeba surrounds a bacterium (or other microorganism) with its pesudopods, encases it in a food vacuole, and extracts the needed nutrients. Thus, amoebae can be viewed as professional phagocytes that are similar to macrophages and neutrophils (Chen G, et al. 2007. Science. 317:678-68). Mechanistically, both amoebae and the immune cells capture bacteria by phagocytosis within cytoplasmic vesicles (FIG. 2). These vesicles fuse with lysosomes as a step in the killing of entrapped bacteria. Once amoebae clean an area of bacteria, they then come together and aggregate to form a unit similar to a multi-cellular organism. During the social cycle, thousands of amoebae aggregate in tune to a camp signal and the single cells form a slug. Ultimately the slug develops into spore-laden fruiting bodies (FIG. 3). The social amoebae belonging to the phylum Mycetozoa have been described as primitive eukaryotes that exhibit characteristics found among both protozoans and fungi (Bonner J T. (2009); Raper K B, Rahn A W. (1984) The Dictyostelids). This description can be summarized in an illustration of their asexual life cycle (FIG. 3). Each species of amoeba has a vegetative phase where, as microscopic unicellular protists, independent amoeboid cells feed upon bacteria, grow, and multiply. When the amoebae exhaust their bacterial food source, they enter a social phase in which individual cells stream together to form a multicellular, differentiated, mobile slug. Since growth occurs at the single-cell stage, its size depends on how many amoebae have entered the aggregate, and slugs will vary in length from about 0.2 to 2 millimeters, a ten fold range, and by the latest estimates the number of amoebae they contain ranges from about 10,000 to 2 million. The slug eventually comes to rest and develops into a macroscopic fruiting body consisting of a stalk with sorocarp. Within the sorocarp are environmentally and temporally stable spores, which are disseminated by the wind, animals, or the forces generated by the sorocarp falling. From each viable spore a single amoeba arises Unlike animals or plants, amoebae eat first; then grow by simply producing an increasing number of separate amoebae, and when food (bacteria/fungi) is gone they stream together to become multi-cellular. Once amoebae form their fruiting bodies they can no longer do anything that requires an intake of energy: they are static. The only part of them that is alive is the dormant spores.

In addition to their feeding behavior, amoebae possess many other virtues that are conducive to an amoebic antimicrobial therapy: Most prominent virtues of this group of organisms have been studied and extensively described for *Dictyostelium discoideum*. Although the below discussion in exemplified by *D. discoideum*, the present invention is not limited to a particular strain of amoeba.

*D. discoideum* amoebae and spores themselves are not known to be pathogenic to animals and plants. *D. discoideum* consumes and digests a variety of pathogenic and non-pathogenic bacteria, whether live or dead. Moreover, bacteria that are resistant to conventional antibiotics are consumed by *D. discoideum* (See e.g., Smith M G, et al. 2007. Genes Dev. 21:601-614). *D. discoideum* not only kills free bacteria, but can consume bacteria living as a colony or biofilm (Raper K B. 1984. The Dictyostelids. Princeton University Press. Princeton N.J.). Thus, slime molds further find use in controlling microbial biofilms. In some embodiments, amoeba are prophylactically administered to patients who are at a high risk of infection (e.g. hospitalized burn patients), that risk unacceptable consequences of infections (e.g. after cosmetic surgery), or who are injured in high risk environments like battlefields. As a eukaryotic organism, *D. discoideum* amoeba is not susceptible to anti-prokaryotic antibiotics. Therefore, amoebae can be used in conjunction with most of the antibiotics used to treat bacterial infections.

As a phagocytic agent, amoebae internally digest bacteria. Unlike conventional antibiotics, toxic bacterial products are contained and digested within cytoplasmic vesicles. Thus, endotoxic shock reactions seen in patients treated with conventional antibiotics are unlikely following amoebic therapy (Prins J M, et al. 1994. Antimicrob Agent Chemother. 38(6): 1211-1218).

In some embodiments, amoebic therapy utilizes overwhelming numbers of amoebae. Locally, these amoebae quickly contain and consume their bacterial prey. The present invention is not limited to a particular mechanism. Indeed, an understanding of the mechanism is not necessary to practice the present invention. Nonetheless, it is contemplated that in the time frame of therapy, resistance to amoebae will be difficult for pathogens to acquire, and spread of resistance will be minimized. Certain bacteria are facultative intracellular pathogens and there are known strain of genetically engineered bacteria, like the benign soil bacterium *Bacillus subtilis* harboring the gene for lysteriolysin 0, can survive within macrophage-like cell line (Bielecki J, et al. 1990. Nature, 345:175-176). However, in combination with more than one amoebae type or in combination with conventional antibiotics, resistance to amoebic therapy can be minimized or eliminated.

I. Amoebae

As described above, embodiments of the present invention provide compositions and methods for treating infection by microorganisms with amoebae. Examples of amoebae suitable for use in embodiments of the present invention include, but are not limited to, amoebae of the phylum Mycetozoa, which include but are not limited to:

DICTYOSTELIUM: *D. laterosorum, D. tenue, D. potamoides, D. minutum, D. gracile, D. lavandulum, D. vinaceofuscum, D. rhizopodium, D. coeruleo-stipes, D. lacteum, D. polycephalum, D. polycarpum, D. polycarpum, D. menorah, D. caveatum, D. gloeosporum, D. oculare, D. antarcticum, D. fasciculatum, D. delicatum, D. fasciculatum, D. aureo-stipes* var. *helveticum, D. granulophorum, D. medusoides, D. mexicanum, D. bifurcatum, D. stellatum, D. microsporum, D. parvisporum, D. exiguum* TNS-C-199, *D. mucoroides, D. sphaerocephalum, D. rosarium, D. clavatum, D. longosporum, D. macrocephalum, D. discoideum, D. discoideum* AX4, *D. intermedium, D. firmibasis, D. brunneum, D. giganteum, D. robustum, D. multi-stipes, Dermamoeba algensis, D. brefeldianum, D. mucoroides, D. capitatum, D. pseudobrefeldianum, D. aureocephalum, D. aureum, D. septentrionalis, D. septentrionalis, D. implicatum, D. medium, D. sphaerocephalum, D. rosarium, D. clavatum, D. longosporum, D. purpureum, D. macrocephalum, D. citrinum, D. dimigraformum, D. firmibasis, D. brunneum, D. giganteum, D. monochasioides, Thecamoeba similis* and POLYSPHONDYLIUM: *P. violaceum, P. filamentosum, P. luridum, P. pallidum, P. equisetoides, P. nandutensis* YA, *P. colligatum, P. tikaliensis, P. anisocaule, P. pseudocandidum, P. tenuissimum, P. pallidum, P. asymmetricum, P. filamentosum, P. tenuissimum, P. candidum*. ACYTOSTELIUM: *A. ellipticum, A. anastomosans, A. longisorophorum, A. leptosomum, A. digitatum, A. serpentarium, A. subglobosum, A. irregularosporum*. ACRASIDE; *A. granulate, A. rosea;* COPROMYXA: *C. protea, C. arborescens, C. filamentosa,* and *C. corralloides;* GUTTULINA (Pocheina) *G. rosea;* GUTTULINOPSIS *G. vulgaris, G. clavata, G. stipitata, G. nivea* (See e.g., Schaap, et al. 2006 Molecular Phylogeny and Evolution of Morphology in the Social Amoebas, Science 27 Oct. 2006: 661-663; Raper K B. 1984. The Dictyostelids. Princeton University Press. Princeton N.J.; each of which is herein incorporated by reference in its entirety).

Experiments conducted during the course of developments of embodiments of the present invention identified strains of soil-borne amoeba that reduce the bacterial loads (*Polyspondillum palidum* Salvador, ibid WS 371A, *D. discoideum* WS 647, *Dictyostelium giganteum* WS142, Turkey 27 (unknown species), *Actyostilium leptosomum* WS 57.6, *Dictyostelium purpureum* WS 321.5, ibid WS 321.7, *Dictyostelium discoideum* X3, WS309, WS 255×281 (hybrid of unknown species), *Dictyostelium lavandullum* Tu4b or *Polispondillum candidum* Fr14; all names, except *D. discoideum* X3, given by K. Raper in his collection of slime molds maintained by and available at the Department of Bacteriology at University of Wisconsin-Madison, USA). In this collection a dichotomous key based on cellular morphology and behavior plus the shape and color of spores, sori, or sorocarp has been used to determine the genus and species of the Mycetozoa (Raper K B, Rahn A W. (1984) The Dictyostelids; Swanson A, Spiegel F, Cavender J. (2002) Mycologia 94: 968-9). Despite origins dating back to the early 1900s, this key holds up remarkably well when amoebae are examined using modern molecular techniques. For example, a multiple loci DNA sequence comparison revealed extensive genetic variation among Dictyostelid species (Schaap et al., (2008) Molecular phylogeny and evolution of morphology in the social amoebas. Science 314 (5799): 661-3). In addition to confirming the ontological method of classifying the social amoeba, these differences indicate that different species can have unique genetic traits.

The amoebae described herein have evolved to consume a myriad of species of bacteria that live in soil communities. Like macrophages and neutrophils, single celled amoebae chase, engulf and digest their microbial prey (Chen G, Zhuchenko 0, Kuspa A. (2007) Science 317(5838): 678-81). Amoebae readily consume planktonic bacteria. In addition, they likely have acquired the ability to eat bacteria within biofilms because amoebae thrive within biologically complex and environmentally harsh soil bio-webs (Rodriguez S, Bishop P. (2007) Three-dimensional quantification of soil biofilms using image analysis. Environ Eng Sci 24(2): 96-103).

The existence of soil amoebae has been known for almost one hundred and fifty years (Brefeld O. (1869) Abh. Seckenberg Naturforsch. Ges. 7: 85-107). But it was not until 1965, when Cavender and Raper (Cavender J C, Raper K B. (1965) Am J Bot 52: 294-6) developed a quantitative method for their enumeration, that extensive ecological studies of these organisms were undertaken. For the best-characterized genus, *Dictyostelium*, nine species were found to be common inhabitants of the upper soil and leaf litter layers in the forests of North America (Cavender J C, Raper K B. (1965) The Acrasieae in nature. I. Isolation. Am J Bot 52: 294-6). Since the publication of these early studies, it has been shown that the Dictyostelids occur worldwide in a variety of soil environments (Swanson A, Vadell E, Cavender J. (2001) Global distribution of forest soil dictyostelids J Biogeo 26(1): 133-48). Collectively, the ecological studies suggest that amoebae are truly cosmopolitan both with regard to their geographic distribution and ecological niches.

In some embodiments, *D. discoideum* isolates are utilized. Strains of amoebae have been isolated that grow on bacteria and on synthetic media (Sussman M, 1966. Biochemical and genetic methods in the study of cellular slime mold development. pp. 397-410. In: Methods in Cell Physiology, Vol. 2, Edited by D Prescott. Academic. Press, New York). High numbers of organisms are easily obtained; Chemical and transposon mutagenesis is routinely used with amoebae to isolate growth and functional mutants (Liwerant I J & Pereira da Silva L H. 1975. Mutat Res. 33(2-3):135-46); Barclay S L & Meller E 1983. Mol Cell Biol. 3:2117-2130). *D. discoideum* is a haploid easing the genetic characterization of mutant organisms; the genome sequence of *D. discoideum* has been determined and published (Eichinger L, et al. 2005. Nature. 435:43-57). Also, that genome was recently compared to the genome of the genomes sequence of *D. purpureum* (R. Sucgang et al., 2011, Genome Biology 2011, 12).

In some embodiments, amoeba therapy utilizes *D. discoideum* isolate AX-3, but is not limited to this axenic strain. AX-3 isolate has the novel, and useful, property of axenic growth; that is, growth on media without a bacterial food supply. Historically, AX-3 is pre-dated by other axenic mutants. Repeated sub-culturing of wild type *D. discoideum* in a liquid medium containing salts, liver extract, and fetal calf serum was used to obtain archetype axenic strains. Using this technique, Sussman and Sussman isolated AX-1, the first reported axenic mutant (Sussman R & Sussman M. 1967. Biochem. Biophys. Res. Commun 29:53-55). Based the previous studies, Loomis isolated a N-methyl-N'-nitro-N-nitrosoguanidine (MNNG) mutant that is capable of axenic growth in chemically defined media (Loomis, W F Jr. 1971. EXDI Cell Res. 64, 484-486). This strain, named AX-3, has at three genetically-defined mutations that confer the growth phenotype (Williams K L et al. 1974. Nature, London 247, 142-143; North M J & Williams K L. 1978. J. Gen. Microbiol. 107:223-230). As a basis for amoebic therapy, propagation of *D. discoideum* in bacteria-free cultures is a strong advantage. Axenic cultures can be used to manufacture the large numbers of pathogen-free amoebae or spores that are needed for therapy.

Advantageous phenotypes can be linked to multiple genetic mutations, and these mutations can be serially selected using multiple rounds of MNNG mutagenesis. Most questions concerning amoebic therapy can be addressed by manipulating of the amoeba's genome. Amoeba can be genetically altered by chemical mutagenesis or with molecular techniques. For example, *D. discoideum* is a haploid organism. Its genome sequence is published and mutants are easily generated by chemical mutagenesis, gene replacement technologies, and by RNA interference (Barclay S L & Meller E. 1983. Mol Cell Biol. 3:2117-2130; Eichinger L, et al. 2005. Nature. 435:43-57).

In some embodiments, amoebae are stored and/or transported in the spore stage of the life cycle. *D. discoideum* forms easily germinated temperature-, environment-, and temporally-stable spores. In the absence of a bacterial food supply, essential amino acids become limiting, and *D. discoideum* sporulates. Spores have been shown to remain viable, without refrigeration, for over 50 years when lyophilized or stored in silica gel. When nutrients are available, spores germinate in 6-10 hours to produce amoebae. Spores can be exploited as a means of transport and storage of medicinal amoebae. For convenience, spores can be administered embedded in bandages or dressings, gels, etc.

In some embodiments, the present invention provides kits and/or compositions comprising amoebae. In some embodiments, amoebae are in a form (e.g., spores) that is stable for long term storage. In other embodiments, amoebae are stored and transported in different stages. In some embodiments, compositions comprise additional components (e.g., storage reagents, buffers, preservatives, stabilizers, etc.). In some embodiments, amoeba or spores are stored or transported at 80° C. in 10% Dimethyl sulfoxide (DMSO) or 10% glycerol, in the MS2 medium comprising the following: peptone 10 g, dextrose 10 g, $Na_2HPO_4 \times 12 H_2O$ 1 g, $KH_2PO_4$ 1.5 g, $MgSO_4$ 0.5 g, per 1 L, 1 g yeast extract (Raper 1984). Another method of long-term storage of spores is liophylization. In other embodiments, amoebae or spores are stored short-term at 4° C. in medium MS2 solidified with 10 g of agar per L.

In some embodiments, the present invention also provides pharmaceutical preparations for treating microbial infections in clinical, agricultural, research and industrial applications. In certain clinical applications, these preparations comprise one of the aforementioned amoebae/slugs or spores (FIG. 3), formulated for an administration to the patient. In some embodiments amoebae, slugs or spores are incorporated into bandages, dressings, or other wound coverings. In addition, in some embodiments, spores are incorporated into salves, ointments, or other topical applications.

In some embodiments, amoebae, slugs or spores are delivered by pharmaceutically acceptable carrier, that refers to any of the standard pharmaceutical carriers including, but not limited to, saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For example, of carriers, stabilizers, and adjuvants. (See e.g., Martin, Remington's Pharmaceutical Sciences, 15th Ed., Mack Publ. Co., Easton, Pa. (1975), incorporated herein by reference). Moreover, in certain embodiments, the compositions of the present invention may be inoculated for horticultural or agricultural use. Such formulations include dips, sprays, seed dressings, stem injections, sprays, and mists.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration (e.g., to tissues, wounds, organs, etc) may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

Dosing is dependent on severity and responsiveness of the disease state or condition to be treated, with the course of treatment lasting from several days to several months, or until a cure is effected or a diminution of the disease state is achieved. In some embodiments, treatment is administered in one or more courses, where each course comprises one or more doses per day for several days (e.g., 1, 2, 3, 4, 5, 6) or weeks (e.g., 1, 2, or 3 weeks, etc.). In some embodiments, courses of treatment are administered sequentially (e.g., without a break between courses), while in other embodiments, a break of 1 or more days, weeks, or months is provided between courses. In some embodiments, treatment is provided on an ongoing or maintenance basis (e.g., multiple courses provided with or without breaks for an indefinite time period). Optimal dosing schedules can be calculated from measurements of drug accumulation in the body of the patient. The administering physician can readily determine optimum dosages, dosing methodologies and repetition rates.

II. Uses

Embodiments of the present invention provide compositions and methods for the therapeutic, clinical, research, agricultural and industrial use of amoebae. Exemplary applications are discussed herein. Additional uses are known to one of ordinary skill in the art.

A. Clinical and Therapeutic Applications

In some embodiments, amoebae are used in the treatment of subjects (e.g., humans or non-human animals) infected with a microorganism (e.g., pathogenic bacteria). In some embodiments, amoebae are used on infected skin wounds. At sites suffering tissue damage and infection, amoebae will consume large numbers of pathogens. This feeding behavior reduces the bacterial load sufficiently for wounds and surgical closures to heal naturally, and for grafts to thrive.

Chronically infected wounds present a significant burden to the healthcare system both in terms of individual and societal costs. Two important factors hamper successful treatment of these wounds: The lack of unified criteria for employing different treatments and the lack of proven treatment regimens. Against this backdrop of variability, the idea that a critical microbial load is a principal determining factor in wound healing has fared remarkably well. Numerous studies have demonstrated that the microbial load is a reliable predictive indicator of successful treatment outcomes (Bendy et al., (1964) Antimicrob. Agents Chemother (Bethesda) 10: 147-55; Bergstrom et al., (1994) Treatment of pressure ulcers. Clinical practice guideline, No. 15; Bowler P G. (2002) Wound pathophysiology, infection and therapeutic options. Ann Med 34(6): 419-27; Krizek T J, Robson M C. (1975) Am J Surg 130(5): 579-84; Robson M C, Heggers J P. (1969) Mil Med 134(1): 19-24; Daltrey et al., (1981) J Clin Pathol 34(7): 701-5. PMCID: PMC493797; Dow G. (2001) Infection in chronic wounds. Chronic Wound Care: A Clinical Source Book for Healthcare Professionals: 343-56). These studies all discuss that $10^5$ organisms per gram of tissue is the breakpoint beyond which wounds become non-healing. The best current practices aim at keeping the localized concentration of bacteria in wounds well below this threshold, typically through the administration of systemic antibiotics and surgical debridement (Bowler P G., 2002, Ann Med 34(6): 419-27). The treatment of chronic infections of the skin often is a challenge to clinicians. Infected, burns, surgical wounds, and diabetic lesions can be refractory to current treatment regimes causing them to persist as open sores. The most common underlying reasons for this type of pathology are: antibiotic failure due to high bacterial loads, infection with multiple antibiotic-resistant pathogens, or the formation of antibiotic-impervious biofilms. Clinicians are demanding new and more effective therapies.

Recently, owing to the frequency of therapeutic failures, there has been growing interest in the development and use of topical antimicrobial agents. Biotherapeutics for disease can be found in bacteriophage, bacterial interference, and leech and maggot therapies. For instance, bacteriophage therapy, as an alternative or adjunct to chemical antibiotics, has been advanced in Eastern Europe. Presently, this strategy is receiving renewed attention in Great Britain and in the United States. Phage therapy uses mixtures of lytic viruses to kill pathogenic bacteria (Mann N H, 2008. Res Microbiol. 159: 400-405). A second strategy, bacterial interference, uses live benign bacteria to displace pathogenic organisms. Several examples of this technology are in the research stage (Huovinen P. 2001. BMJ. 323:353-354, and U.S. Pat. No. 6,991,786). The US Food and Drug Administration has approved both leeches and maggots as Class II medical devices. Leeches are used in the treatment of venous congestion (Zhang X, et al. 2008. J Hand Surg Am. 33:1597-601), and maggots are used to disinfect and debride wounds (Hunter S, et al. 2009, Adv Skin Wound Care. 22:25-27).

The use of biologics is much broader than those examples mentioned above. For example, preparations of the prokaryote *Lactobacillus acidophilus* for use in human therapies is known (see, e.g., U.S. Pat. Nos. 5,032,399 and 5,733,568). In addition, pharmaceutical preparations of *Lactobacillus acidophilus* are known (See e.g., U.S. Pat. No. 4,314,995). Additional applications of biologics in human therapy are described in U.S. Pat. Nos. 5,607,672 (Using recombinant *Streptococcus mutans* in the mouth to prevent tooth decay); U.S. Pat. No. 6,447,784 15 (Genetically modified tumor-targeted bacteria (Salmonella) with reduced virulence); U.S. Pat. No. 6,723,323 (*Vibrio cholerae* vaccine candidates and method of their constructing); U.S. Pat. No. 6,682,729 (A method for introducing and expressing genes in animal cells is disclosed comprising infecting the animal cells with live invasive bacteria); and U.S. Pat. No. 4,888,170 (relating to a vaccine for the immunization of a vertebrate, comprising: an avirulent derivative of a 20 pathogenic microbe).

In some embodiments, amoebae are utilized in the treatment of microbial infections in mucus membranes (e.g., nostrils, throat, rectum, vagina, etc.), tissues or organs (e.g., urinary tract, etc) or bodily fluids (e.g., blood).

In some embodiments, amoebae are utilized in the treatment of infection by drug or multi-drug resistant bacteria (e.g., methycillin resistant *Staph Aureus* (MRSA) or MDR (multi-drug resistant) *Acinetobacter baumannii*) or dormant persister cells.

Dormant persister cells are tolerant to antibiotics and are largely responsible for recalcitrance of chronic infections. Chronic infections are often caused by pathogens that are susceptible to antibiotics, but the disease may be difficult or even impossible to eradicate with antimicrobial therapy. For many pathogens, including *S. aureus*, a highly significant factor of virulence steams from the fact that in addition to fast-growing cells these pathogens produces small numbers of dormant persister cells whose function is survival in adverse circumstances. Persisters are not mutants, but phenotypic variants of the wild type, and are tolerant to killing by antibiotics. The dormancy protection from antibiotics is mechanistically distinct from genetically determined MRSA. Antimicrobial therapy, however, selects for high persistence mutants, or Small Colony Variants (SCVs). SCVs have been found for many genera of bacteria, but they have been most extensively studied for staphylococci. (Proctor et al., Clin. Infect. Dis. 20, 95-102 (1995). *S. aureus* SCVs can also cause more aggressive infections in both humans and animals. The high rate of selection by aminoglycosides indicates that SCVs are part of the normal life cycle of staphylococci. (Massey et al., Curr. Biol. 11, 1810-1814 (2001). Massey, R. C. & Peacock, S. J. Curr. Biol. 12, R686-R687 (2002).

Experiments conducted during the course of development of embodiments of the present invention demonstrated that soil amoebae can destroy MRSA and persister cells of the pathogen.

In some other embodiments, the present methods and compositions are directed to specifically controlling (e.g., therapeutic treatments or prophylactic measures) diseases caused by the following pathogens: *Bartonella henselae, Borrelia burgdorferi, Campylobacter jejuni, Campylobacter fetus, Chlamydia trachomatis, Chlamydia pneumoniae, Chylamydia psittaci, Simkania negevensis, Escherichia coli* (e.g., O157:H7 and K88), *Ehrlichia chafeensis, Clostridium botulinum, Clostridium perfringens, Clostridium tetani, Enterococcus faecalis, Haemophilus influenzae, Haemophilus ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis* and *Treponema pallidum*.

B. Surfaces

In some embodiments, compositions of the present invention are used to treat surfaces. Surfaces that can be treated by the methods and compositions of the present invention include but are not limited to, surfaces of a medical device (e.g., a catheter, implants, stents, etc.), a wound care device, a body cavity device, a human body, an animal body, a food preparation surface, an industrial surface, a personal protection device, a birth control device, and a drug delivery device. Surfaces include but are not limited to silicon, plastic, glass, polymer, ceramic, skin, tissue, nitrocellulose, hydrogel, paper, polypropylene, cloth, cotton, wool, wood, brick, leather, vinyl, polystyrene, nylon, polyacrylamide, optical fiber, natural libers, nylon, metal, rubber, soil and composites thereof. In some embodiments, the treating destroys growing, nongrowing, or dormant microbial pathogens.

C. Agricultural Uses

In some embodiments, amoebae are used in the treatment of microbial infections of agricultural and industrial plants. For example, in experiments conducted during the course of developments of embodiments of the present invention amoebae were shown to be effective against virulent strains of *Erwinia amylovora* (88, 85.1 and A97.1) a causative agent of Fire blight in fruit crops. In addition, *Burkholderia cepacia* is a bacterium which produces economic losses to onion crops (Burkholder 1950. Phytopathology 40:115-118).

D. Biofilms

In some embodiments, the methods and compositions of the present invention target bacteria present as a biofilm. Biofilms can be broadly defined as microbial cells attached to a surface, and which are embedded in a matrix of extracellular polymeric substances produced by the microorganisms. Biofilms are known to occur in many environments and frequently lead to a wide diversity of undesirable effects. For example, biofilms cause fouling of industrial equipment such as heat exchangers, pipelines, and ship hulls, resulting in reduced heat transfer, energy loss, increased fluid frictional resistance, and accelerated corrosion. Biofilm accumulation on teeth and gums, urinary and intestinal tracts, and implanted medical devices such as catheters and prostheses frequently lead to infections (Characklis W G. Biofilm processes. In: Characklis W G and Marshall K C eds. New York: John Wiley & Sons, 1990:195-231; Costerton et al., Annu Rev Microbiol 1995; 49:711-45).

Biofilm formation is a serious concern in the food processing industry because of the potential for contamination of food products, leading to decreased food product quality and safety (Kumar C G and Anand S K, Int J Food Microbiol 1998; 42:9-27; Wong, J Dairy Sci 1998; 81:2765-70; Zottola and Sasahara, Int J Food Microbiol 1994; 23:125-48). The surfaces of equipment used for food handling or processing are recognized as major sources of microbial contamination. (Dunsmore et al., J Food Prot 1981; 44:220-40; Flint et al., Biofouling 1997; 11:81-97; Grau, In: Smulders F J M ed. Amsterdam: Elsevier, 1987:221-234; Thomas et al., In: Smulders F J M ed. Amsterdam: Elsevier, 1987:163-180). Biofilm bacteria are generally hardier than their planktonic (free-living) counterparts, and exhibit increased resistance to antimicrobial agents such as antibiotics and disinfectants. It has been shown that even with routine cleaning and sanitizing procedures consistent with good manufacturing practices, bacteria can remain on equipment, food and non-food contact surfaces and can develop into biofilms. In addition, *L. monocytogenes* attached to surfaces such as stainless steel and rubber, materials commonly used in food processing environments, can survive for prolonged periods (Helke and Wong, J Food Prot 1994; 57:963-8). This would partially explain their ability to persist in the processing plant. Common sources of *L. monocytogenes* in processing facilities include equipment, conveyors, product contact surfaces, hand tools, cleaning utensils, floors, drains, walls, and condensate (Tomkin et al., Dairy, Food Environ Sanit 1999; 19:551-62; Welbourn and Williams, Dairy, Food Environ Sanit 1999; 19:399-401).

Bacterial growth and survival in the environment as well as in association with human hosts are constrained by the action of phagocytic eukaryotic cells. Phagocytic predation on bacteria by host immune cells shares a number of cellular mechanisms with free-living protozoa. In and outside the human host, bacteria growing in biofilms appear to be less vulnerable to phagocytic predators than planktonic cells. Widespread resistance against predators is mediated by the interplay of biofilm-specific traits such as substratum adherence, exopolymer production, cellular cooperation, inhibitor secretion, and phenotypic variation.

An important mortality factor in the control of bacterial populations is the uptake and killing of bacteria by phagocytic eukaryotic cells (See e.g., Matz, Biofilms and Predations, 194-213 in The Biofilm Mode of Life: Mechanisms and Adaptations, Horizon Bioscience Editor: Staffan Kjelleberg and Michael Givskov, June 2007; herein incorporated by reference in its entirety). Accordingly, embodiments of the present invention provide compositions and methods for the use of amoebae in the killing of bacteria present in biofilms.

E. Combination and Co-Therapy

In some embodiments, compositions for use in killing microorganisms utilize two or more distinct species of amoebae. Some species of amoebae use different chemoattractants while other species use the same attractants. For example, for *D. mucoroides* it is cyclic AMP, while that of *P. violaceum* is a dipeptide called glorin. This means that when the aggregation centers are first formed, each species is producing its own attractant and will attract only the amoebae that respond to it; they will have no interest in the attractant of the other species and therefore no possibility of commingling.

In another case, Raper and Thom chose two species that had the same chemoattractant, which is cyclic AMP (Raper, K. B., and C. Thorn (1941) Am. J. Botany 28: 69-78). Strains were *D. mucoroides* with white sori and *D. purpureum* with purple sori. The authors found that these two species co-aggregated into common centers, but there was a surprising sequel. Fruiting bodies arose from the same mound and their sorocarps were either white or purple: the amoebae had separated into two groups in the mound, and the resulting fruiting bodies were pure and all their amoebae were of either one species or the other.

Yet in another case, H. Hagiwara (Hagiwara, H. (1989) The taxonomic study of Japanese Dictyostelid cellular slime molds. Tokyo: National Science Museum Press) discovered a strain of *P. pallidum* that produces a substance that destroys many other strains of *P. pallidum* as well as a common wild-type strain *D. discoideum*. They do so by secreting a lethal molecule that devastates the amoebae of the susceptible victim.

Thus, in some embodiments, two or more compatible species are utilized in a composition. Such combinations are contemplated to find particular use in the killing of drug resistant microorganisms and mixed populations of microorganisms.

In some embodiments, one or more amoebae are administered in combination with known anti-microbial agents. There are an enormous amount of antimicrobial agents currently available for use in treating bacterial and fungal. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); and antimetabolites (e.g., trimethoprim and sulfonamides). Various combinations of antimicrobials may be employed.

EXPERIMENTAL

The following examples are provided in order to demonstrate and further illustrate certain preferred embodiments and aspects of the present invention and are not to be construed as limiting the scope thereof.

Example 1

Methods

The idea of amoebic therapy is unorthodox. Various publications report the typical growth conditions for amoebae isolates: solid media composed of natural product extracts, soil bacteria (food source), and 22° C. incubation at atmospheric oxygen (Raper K B, Rahn A W. (1984) The Dictyostelids). In some embodiments, wounded tissue is at an elevated temperature (Ring E F J. 1986). Bioeng Skin 2(1): 15-30; Forage A V. (1964) Br J Plast Surg 17: 60-1; McGuiness W, Vella E, Harrison D. (2004) J Wound Care 13(9): 383-5) or hypoxic (Mathieu D. (2006) Int J Low Extrem Wounds 5(4): 233-5) or it may contain serum components that neutralize the amoebae (Ferrante A. (1991) Parasite Immunol 13(1): 31-47). Wound conditions are somewhat ill-defined and most likely vary with the type of wound. In such embodiments, culture conditions and choice of amoebae are optimized to match the intended use. In early studies that investigated the ability of *D. discoideum* to consume different bacteria, only one out of the hundred species of bacteria tested was not consumed. Instead, that species killed the amoebae (Raper et al. (1939) J Bacteriol 38(4): 431-45). More recent studies of bacterial pathogenesis that were also limited to *D. discoideum* found a few other species of bacteria that act in this same manner (e.g. species of *Legionella, Pseudomonas* and *Mycobacterium*) (Matz (2005) Trends Microbiol 13(7): 302-7).

Prior to the experiments described below, there appears to have been very little interest in examining the factors that affect the vegetative growth of soil-borne amoebae. As an endpoint, most growth studies enumerated sorocarps, the product of a completed asexual cycle (Raper K B. (1956) Mycologia 48(2):160-205; Raper (1984) The Dictyostelids; Singh B N. (1947) J Gen Microbiol 1(1): 11-21). However, amoebic therapy is primarily concerned with the viability and feeding behavior of vegetative amoebae; their social behaviors are not required for therapeutic applications.

In initial experiments, it was determined if randomly selected strains of slime molds, *D. dictyostelium* being a minority of the isolates, from the K. Raper Archive (WS 57.7; WS 645; WS 255×281; WS 142; WS 309; FR14; Salvador; Tu4b; X3; WS 321.5; WS 321.7; WS 371A; Turkey27) can consume well-studied medical and agricultural pathogens. All amoebae described in the experimental section are available from Dr. Marcin Filutowicz, Department of Bacteriology, University of Wisconsin, Madison. These studies were done under several proxy conditions for wound infection (e.g. temperature, light, pH, presence of serum, oxygen concentration) agricultural virulence (temperature, oxygen etc.). The bacterial species employed in the work were all clinical/field isolates of common pathogens (e.g., *Klebsiella pneumoniae, Staphylococcus aureus* (including its MRSA derivative), *Erwinia amylowora, Pseudomonas syringie*). The screens identified a group of amoebae that consume all tested pathogens under the proxy conditions, thus making them suitable for biotherapeutic uses. Preferred candidates are those which most vigorously devour the test bacteria—in other words, the amoebae producing the largest clearing zones on lawn of specific bacteria. For example, to meet the therapeutic criteria, the amoebae should have the ability to: consume the test bacteria, whether growing or not growing, grow/divide at the elevated temperature, grow/divide under hypoxic conditions, and grow/divide in the presence of sera.

Figure 4:
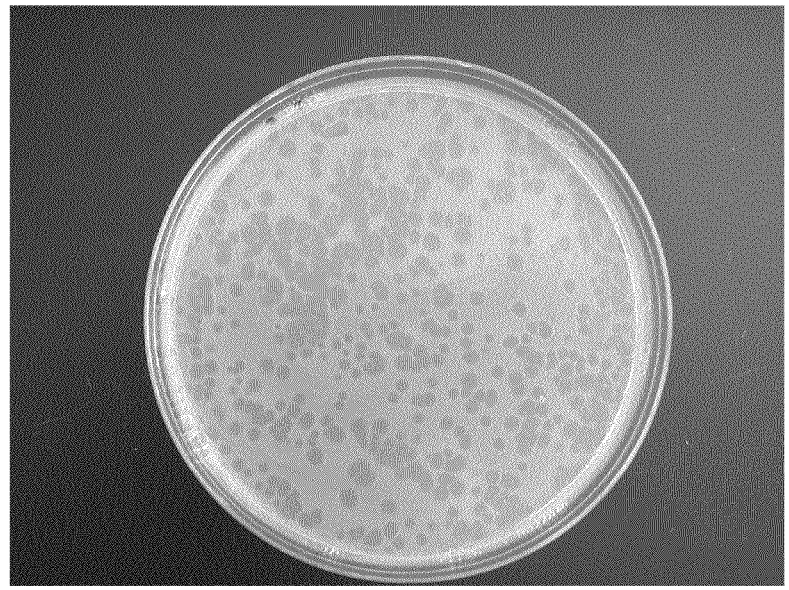
FIG. 4 shows a photograph of killing of bacteria by amoebae; formation of clearing zones also known as "plaques.".

Petri-Dish Assay for the Efficiency of Amoebic Feeding and Development:

To identify putative therapeutic amoebae, a Petri-dish growth assay was used. This assay resembles a bacteriophage growth and enumeration assay in which mixtures of phage and susceptible bacteria are co-cultured as monolayers on solid medium. Each bacteriophage-infected cell gives rise to a clear plaque within the lawn of bacteria. As seen in FIGS. 1 and 4, similar zones of clearing are observed when WS646 amoebae are co-cultured with bacteria. In this work, mixtures of amoebae (or spores) and test pathogens are co-cultured on solid medium (bacterial lawns) or resuspended in semi-solid agar. If the amoebae digest the pathogens, plaques or clearing zones appear on the lawn as the amoebae consume the bacteria. The size of the clear zones is recorded as a measure of the rate of amoebic feeding (compare FIG. 1 and FIG. 4).

Bacterial pathogens were grown in SM2 broth (e.g., *E. amylovora*) or other growth supporting medium (e.g. Tryptic Soy Broth, *S. aureus*) and organisms were removed from the medium by centrifugation. The bacterial cell pellets from these cultures were then plated on the surface of solid medium or resuspended in pre-warmed semi-solid medium (containing 0.6-1% agar). Then spores or amoebae themselves were spotted on lawns of test bacteria and after incubation (e.g., at a desired temperature, presence/absence of serum) photographed without or with magnification, and with or without a light diffuser, using various types of photographic equipment (indicated in the FIG. legends and below). In some experiments microaerophylic conditions were created using microbiological tubes containing growth supporting microbiological media. In other experiments involving agricultural pathogens (e.g. *E. amylovora*), pathogens were grown in SM2 semi solid medium, which was impregnated with a pear slice or supplemented with a homogenized pear according to the established protocols (Vanneste, et al. 1990 J. Bact., 1990, p. 932-941 Vol. 172; Won-Sik Kim et al., Microbiology (2004), 150, 2707-2714).

Example 2

Pairwise Employment of More than One Strain of Amoebae

Figure 5:
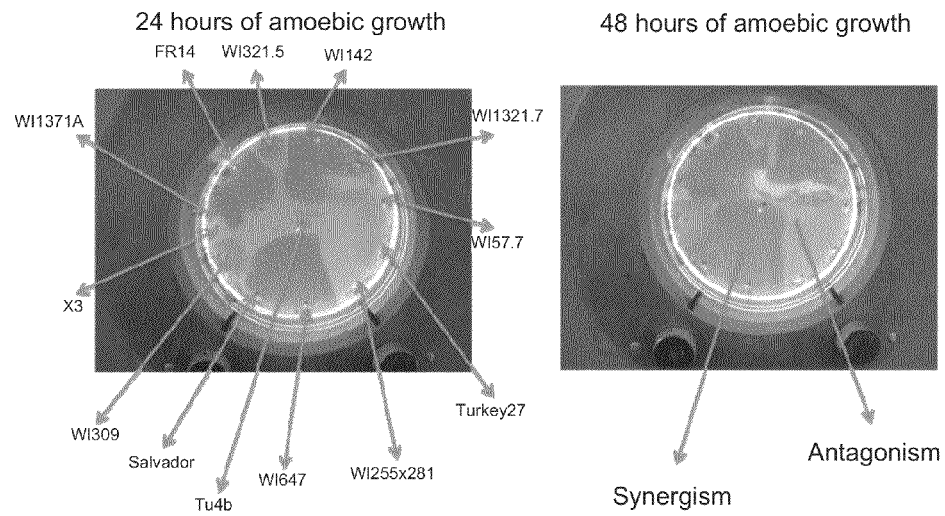
FIG. 5 shows synergism versus antagonism between various kinds of amoebae feeding on *K. pneumonia*.

This example describes the used of two or more types of amoebae to assure that the treated surface/tissue becomes microorganism-free (other than the presence of amoebae themselves, or their various social stages of development; e.g. slugs or sorocarps). Relevant to that, intra- and inter-species chemical communications among amoebae are considered and tested to choose right (compatible) partners. As shown in FIG. 5, some amoebae isolates (e.g., Salvador, and WS647 or WI321.7 and WS142) seem totally unaware of each other's presence as evidenced by the overlapping clearing zones they produce. Therefore, their combination is suitable for use in a biotherapeutic cocktail of amoebae. Other amoebae isolates show a very strong antagonistic behavior (e.g. WS255×281 and WS647 or WS321.5 and either FR14 or WS142) as evidenced by the non-overlapping clearing zones they produce.

Example 3

Growth Temperature

In general, amoebae are propagated at a temperature between 21-25° C. (Raper K B. (1951) Q Rev Biol 26(2): 169-90; Raper K B, Rahn A W. (1984) The Dictyostelids). Temperatures above 25° C. can inhibit the growth of many species of amoebae. Such species can be employed in many, perhaps all agricultural applications (e.g., against *E. amylovora* or *P. syringiae*). Although dermatological wounds typically have comparable surface temperatures (between 24-26° C.), they can measure 35° C. or higher (Ring E F J. (1986) Bioeng Skin 2(1): 15-30; Forage A V. (1964) Br J Plast Surg 17: 60-1; McGuiness W, Vella E, Harrison D. (2004) J Wound Care 13(9): 383-5). In published reports, the determination of growth temperatures relied on observing fruiting body formation, not the ability of free-living amoeba to feed on bacteria. Experiments were performed to determine if the observed temperature restriction affects bacteria-consuming amoebae or a developmental step in sorocarp formation. *Klebsiella pneumonia* ($10^5$ cells) was inoculated in Petri dishes using a standard overlay procedure and grown overnight to produce confluent lawns. The overlays were seeded with the indicated strains of amoebae as described in FIG. 9. Plates were incubated at various temperatures (as indicated) and data was recorded at the times shown in the key (Sporulation) and after 84 hours (Clearing). Sorocarps (spore carriers) were photographed using a camera attached to a Zeiss microscope at 8× magnification; for clearing zones, an Olympus camera without magnification was used. Images from the Salvador strain are provided to illustrate phenotypes. It was the only strain in the subset that grew at 37° C. Data on the other strains have been categorized according to the key. As amoebae feed on a bacterial lawn, they grow and multiply. Over time, a zone of clearing is formed and amoebae undergo development into sorocarps. The data demonstrate variability in these phenotypes among the strains tested.

As shown in FIG. 9, amoebae were identified that can grow at temperatures of 30° C. (WS371A, WS321.5, Ws321.7, WS309, WS142, WS255×281) or even 37° C. (Salvador) whereas most of the amoebae tested grew only at room temperature (Tu4b, X3, Turkey 27 WS57.7, FR4, WS647). Such temperature-resistant strains (e.g. Salvador) can prosper on surface of human/animal wounds and nonsterile nostrils or other mucosal surfaces. Therefore, such strains of amoebae are ideal for treating infected wound lesions and other mucosal surfaces.

Example 4

Growth in Hypoxic Conditions

In an infected wound, it is possible that amoebae will encounter hypoxic conditions because of inflammation, edema and compromised vasculature (Mathieu D. (2006) Int J Low Extrem Wounds 5(4): 233-5). Amoebae are known to grow well in the presence of oxygen and have been reported to become quiescent under anaerobic conditions (Bonner J T. (2009) The social amoebae: the biology of cellular slime molds. ix, 144 p.). However, except for a single study on the development of submerged isolates of *D. mucoroides*, the tolerance of amoebae to anoxic environments appears not to have been formally investigated (Sternfeld et al., (1977) Proc Natl Acad Sci USA 74(1): 268-71).

Figure 6:
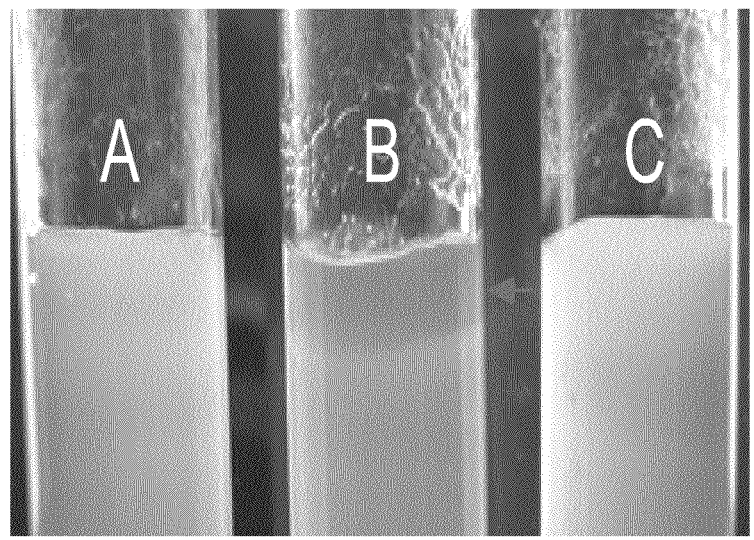
FIG. 6 shows intraspecies variation in amoebic tolerance of hypoxia. Pictured are three tubes containing semi-solid media inoculated with *Klebsiella pneumoniae*. Tube (A) was an amoebae-free control. Tube (B) was co-inoculated with *D. discoideum* WI647. The arrow points to a clear band created as the burrowing amoebae consumed bacteria. Oxygen tension is lower within the medium than at the surface. Tube (C) was co-inoculated with *D. discoideum* X3. This isolate formed plaques on plates seeded with *K. pneumonia*, indicating that the amoebae can feed and are motile, but no band of bacterial clearing was observed in the tube.
Figure 7:
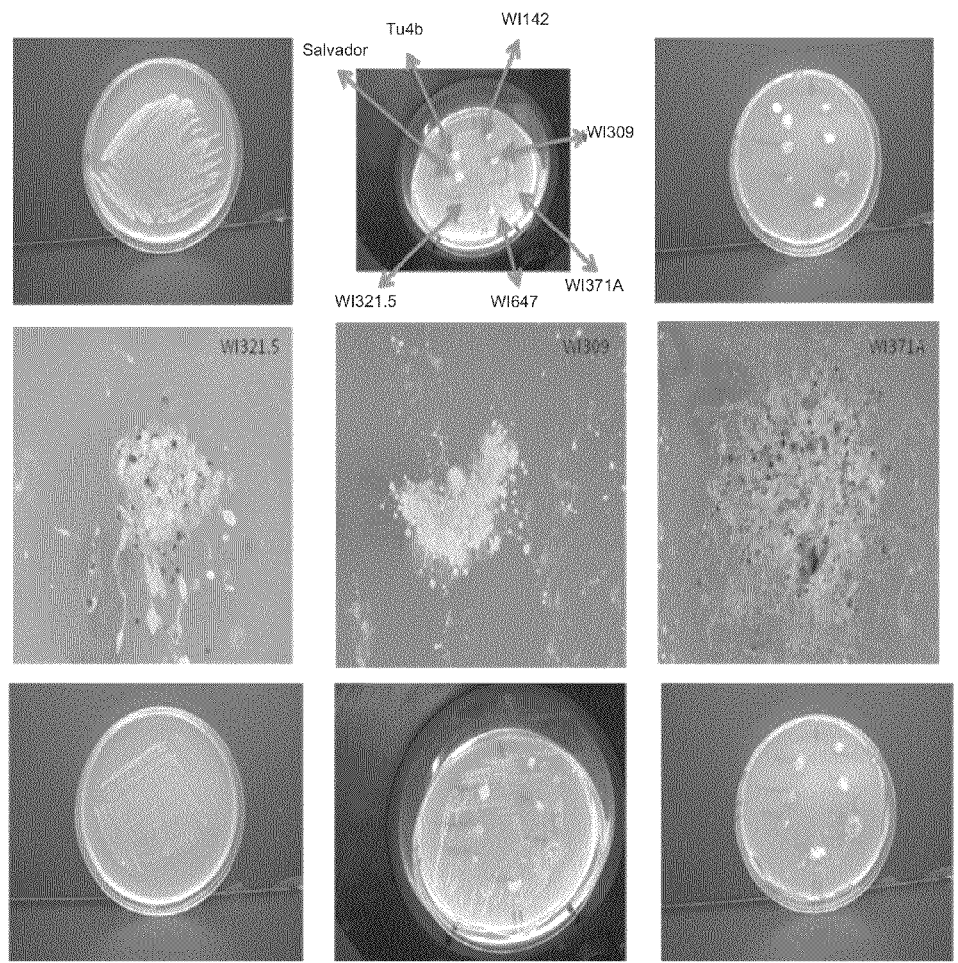
FIG. 7 shows Growth/sporulation of various amoebae on wild-type (top) and menD mutant (bottom) of *S. aureus*. Some amoebae not only feed on bacteria on the plate surface but undergo a full development (middle horizontal panel).

An experiment was performed that tested the ability of amoebae to penetrate throughout top agar seeded with bacteria. As shown in FIG. 6, the results demonstrate that strains differ in their oxygen requirements. WS647 was shown to tolerate microaerophylic conditions. The bacteria on which the amoebae will feed may be embedded in biofilms. If so, oxygen levels may be reduced 1000-fold compared to atmospheric oxygen (Xu et al., (1998) Appl Environ Microbiol 64(10): 4035-9).

Oxygen limitations in the amoebic treatment can also be addressed by the use oxygen-producing dressing on wounds and treated surfaces. This approach has been successfully employed in the therapeutic use of maggots where hypoxia is known to limit therapeutic effectiveness (Sherman R A. (1997) Plast Reconstr Surg 100(2): 451-6).

Example 5

Growth in the Presence of Serum

Toxic amoebae have been shown to be susceptible to serum (Cursons et al., (1980) Infect Immun 29(2): 401-7; Ferrante A. (1991) Parasite Immunol 13(1): 31-47). FIGS. 10-13 demonstrate that selected amoebae isolates can feed on several species of bacterial pathogens in the absence or presence of bovine or porcine sera. Furthermore, they can feed on bacteria re-suspended in media supporting or not supporting their growth.

Figure 10:
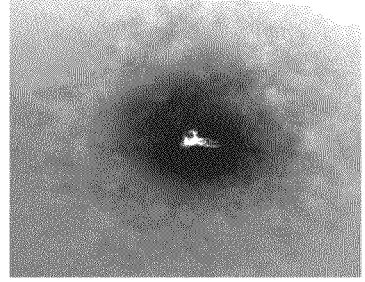
FIG. 10 shows feeding of amoebae on MRSA on non-nutrient agar in the presence of serum.
Figure 10:
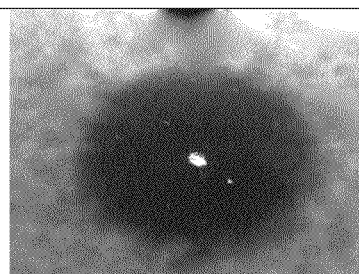
Figure 10:
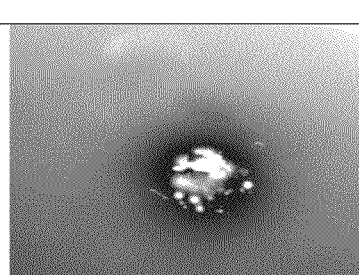
Figure 10:
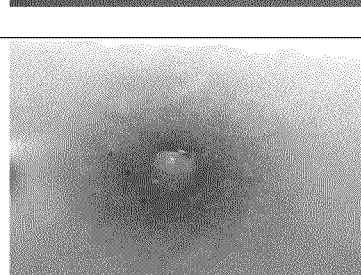
Figure 10:
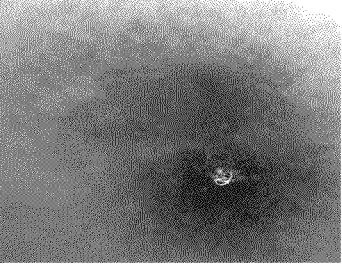
Figure 10:
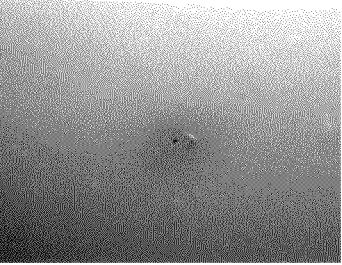
Figure 10:
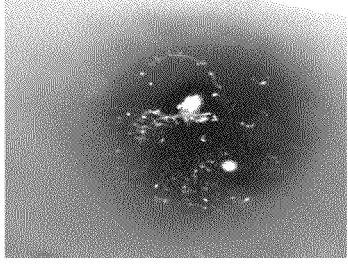
Figure 10:
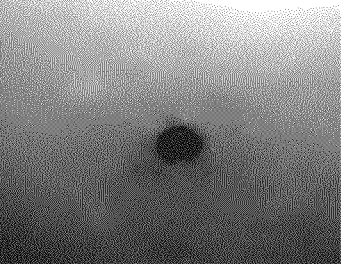
Figure 10:
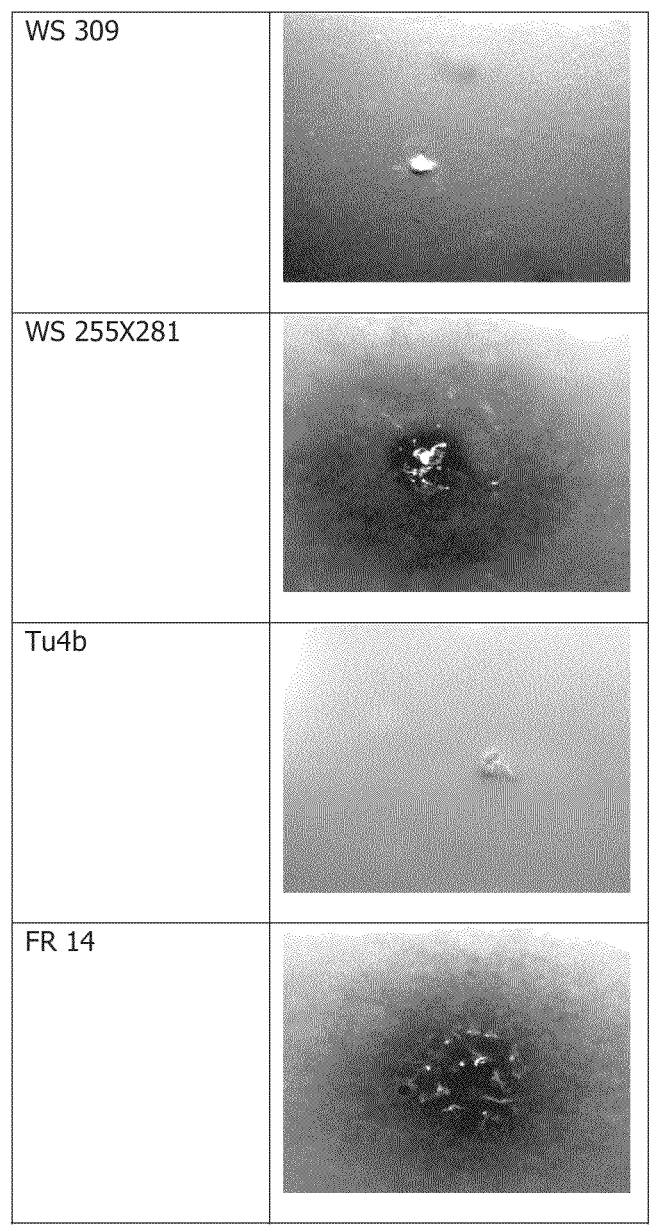

FIG. 10 shows feeding of amoebae on MRSA. The plates were made by using the pathogen grown overnight in TSB medium. Bacteria were peleted and resuspended in semi-solid agar containing bovine serum diluted seven-fold in semi-solid agar supplemented with 0.9% sodium chloride. Plates were incubated at 35° C. and data was recorded after 48 hours. Plates were photographed using a camera attached to a Olympus microscope at 8× magnification. Clearing zones indicate lawns of bacteria destroyed by feeding and dividing amoebae. Structures inside are showing aggregation, slugs and mature fruiting bodies of amoebae with spores. Photos were taken without a light diffuser in the microscope resulting in an enhanced contrast between clearing zones and confluent bacterial growth.

Figure 11:
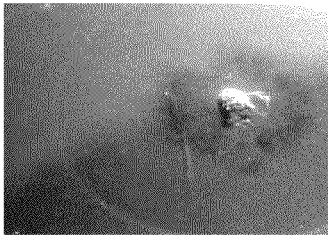
FIG. 11 shows a comparison of the feeding of amoebae on *Klebsiella pneumoniae* with and without serum.
Figure 11:
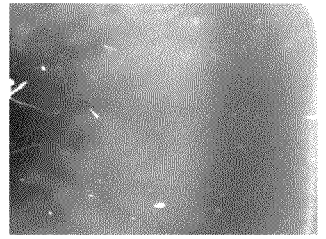
Figure 11:
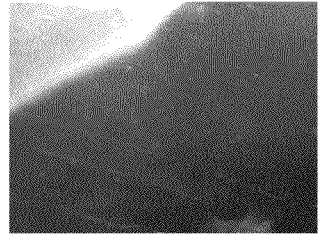
Figure 11:
Figure 11:
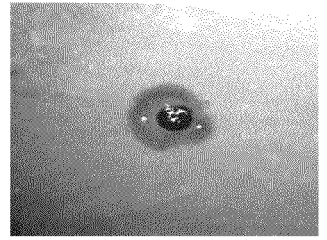
Figure 11:
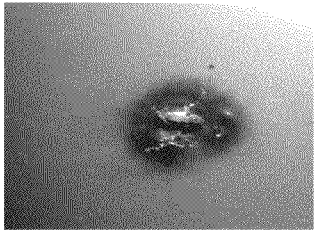
Figure 11:
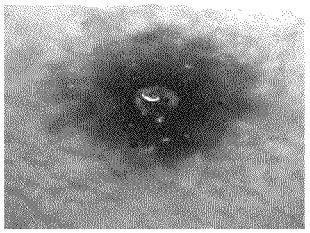
Figure 11:
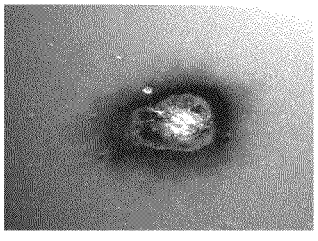
Figure 11:
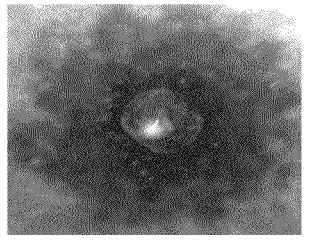
Figure 11:
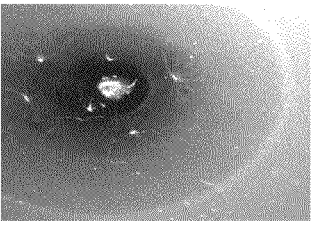
Figure 11:
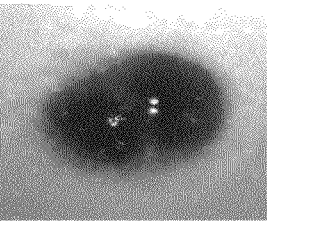
Figure 11:
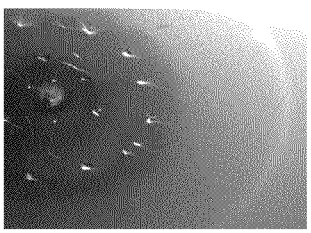
Figure 11:
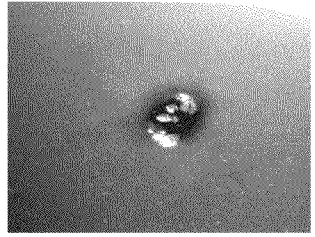
Figure 11:
Figure 11:
Figure 11:
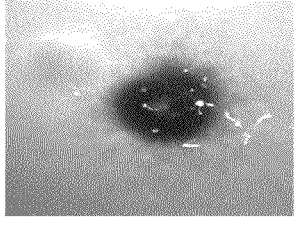
Figure 11:
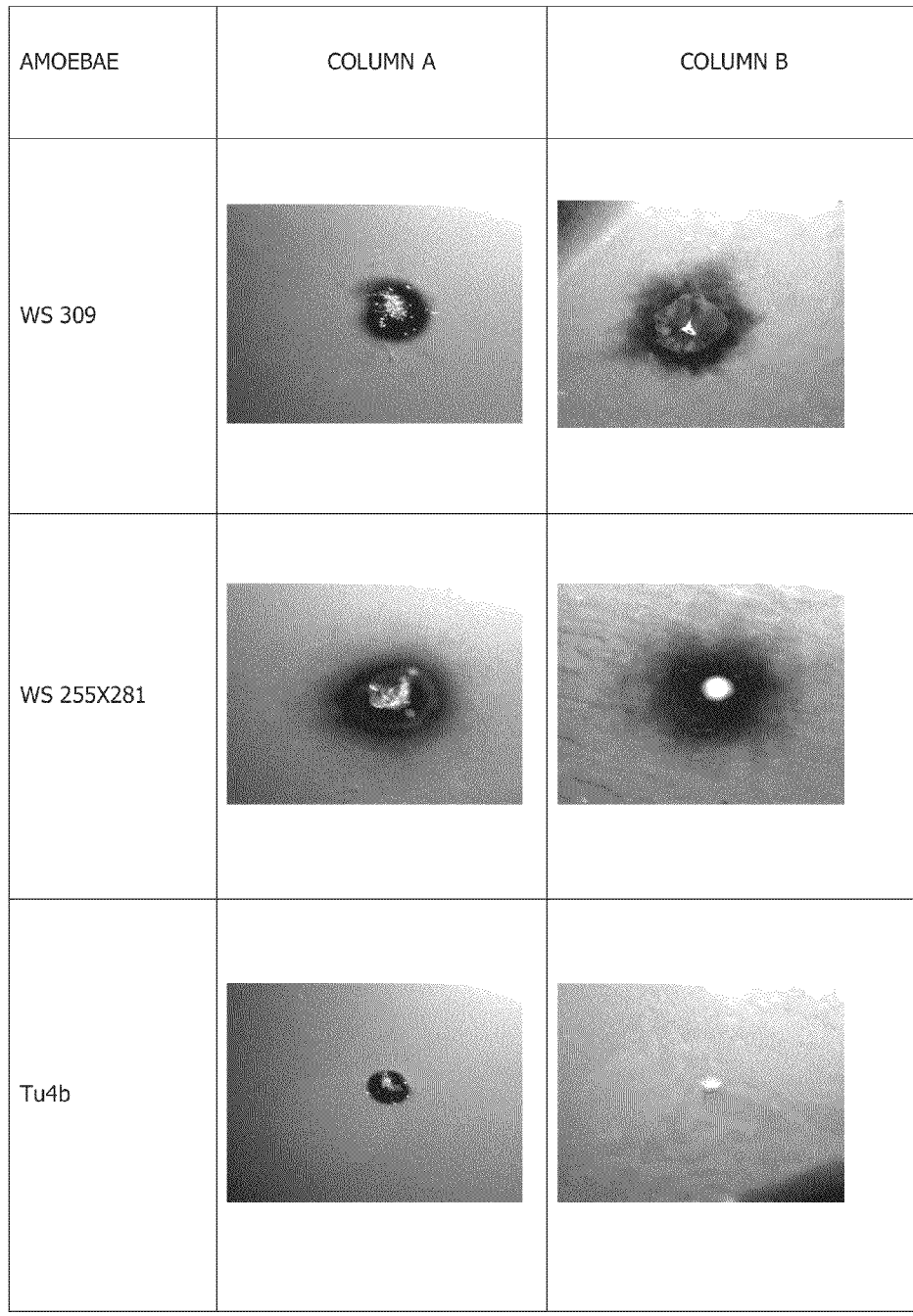
Figure 11:
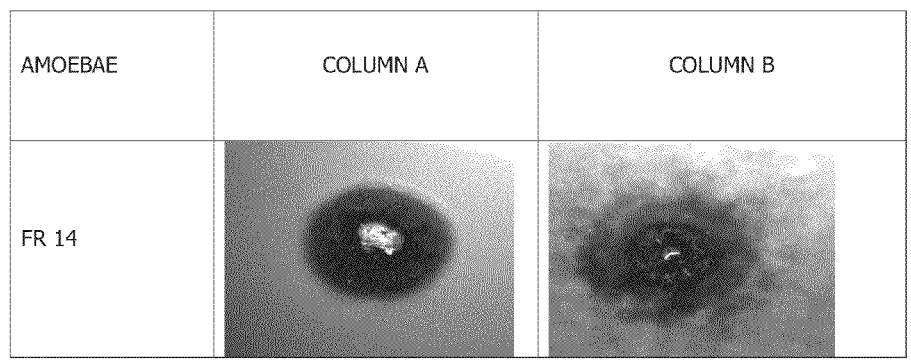

FIG. 11 shows a comparison of the feeding of amoebae on *Klebsiella pneumoniae* with and without serum. Column A shows zones of growth (or lack thereof) of amoebae on plates inoculated with *Klebsiella pneumoniae*. The plates were made by using the pathogen grown overnight in SM2 medium. Bacteria were peleted and resuspended in semi-solid agar containing 0.9% sodium chloride and seven-fold diluted bovine serum (column A) or in semi-solid medium without bovine serum (Column B). Plates were incubated at room temperature and data was recorded after 48 hours (Clearing). Plates were photographed using a camera attached to an Olympus microscope at 8× magnification. Clearing zone shows feeding front of amoebae and structures inside are showing aggregation, slugs and mature fruiting bodies of amoebae with spores.

Figure 12:
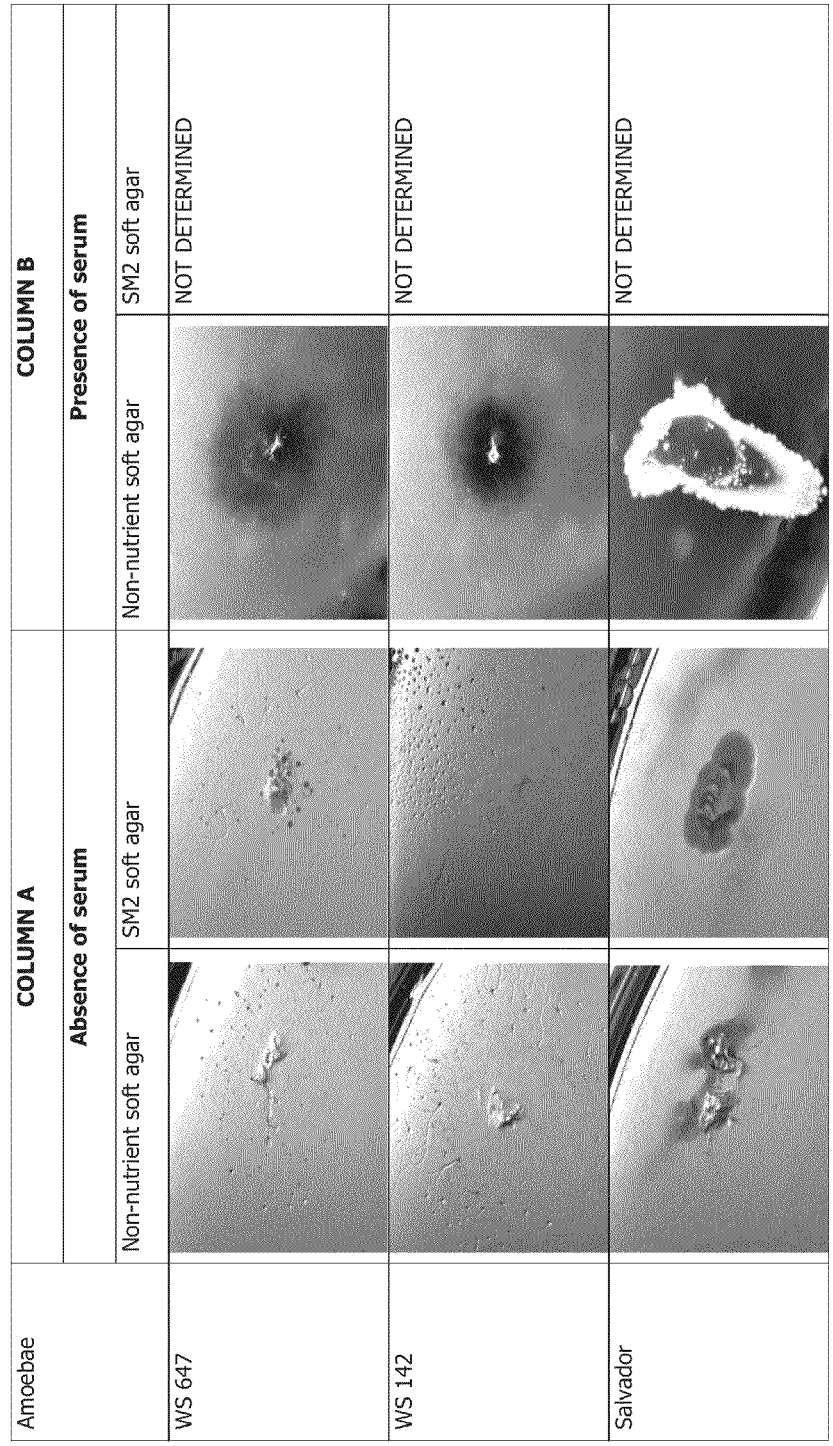
FIG. 12 shows feeding of amoebae on a menD mutant of *S. aureus* in presence and absence of serum.
Figure 12:
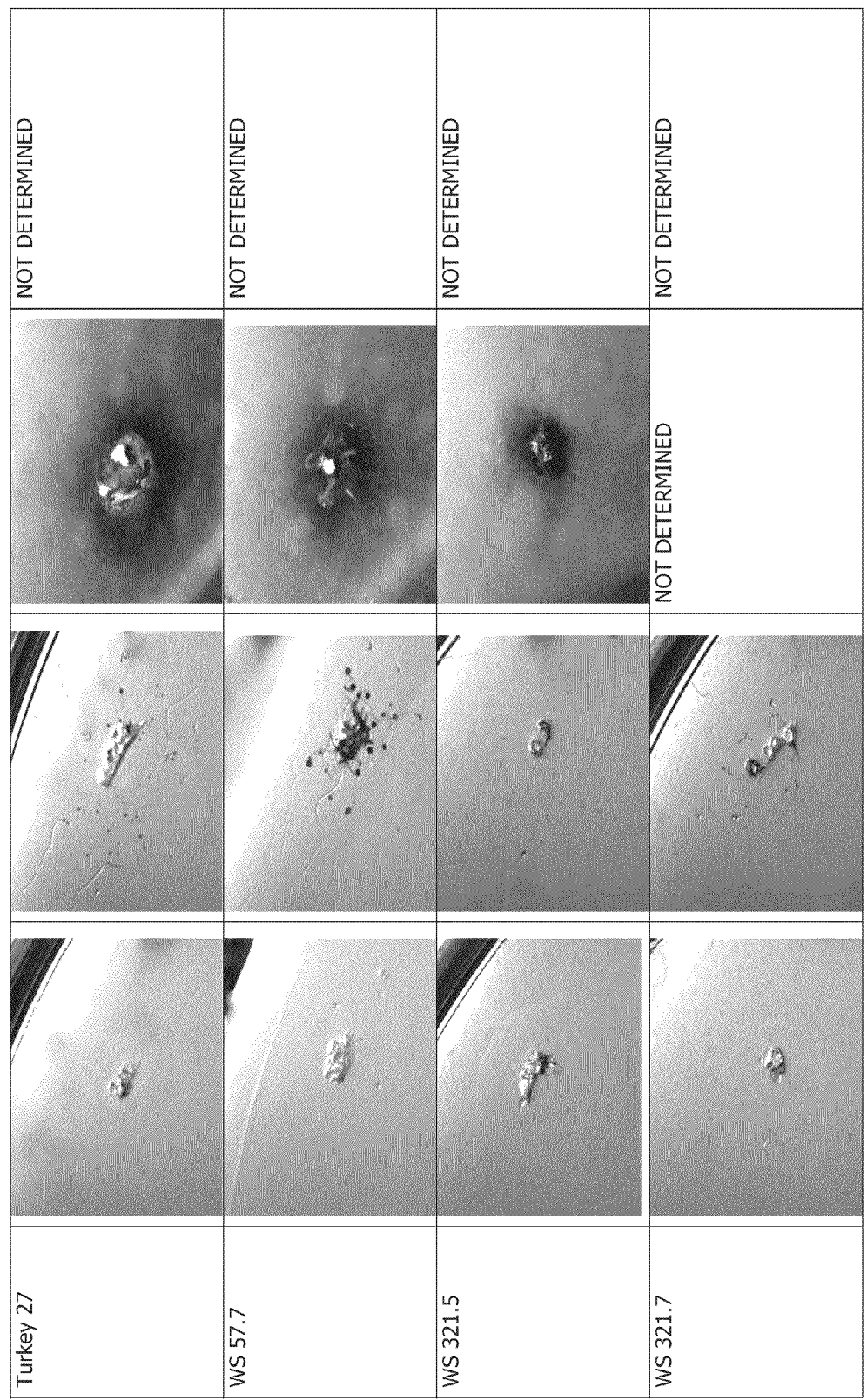
Figure 12:
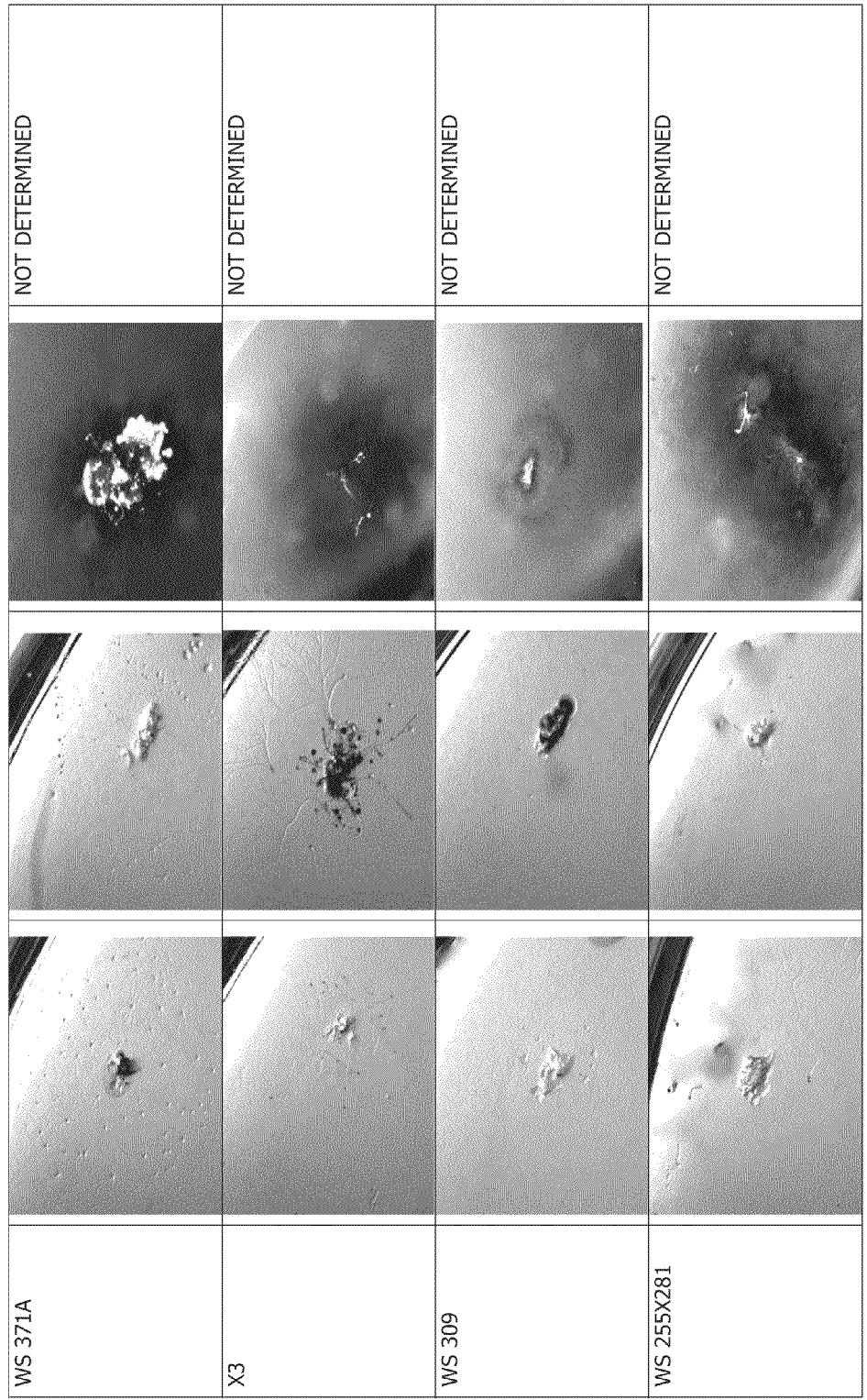
Figure 12:
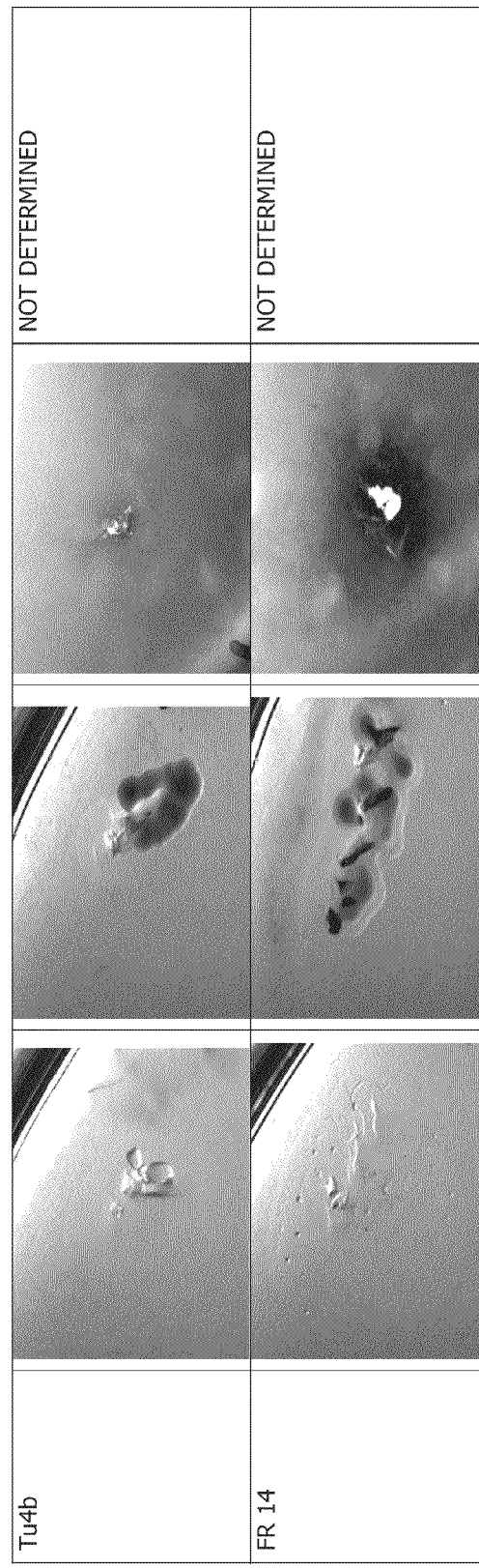

FIG. 12 shows feeding of amoebae on a menD mutant of *S. aureus* in the presence and absence of serum. Shown are pictures of amoebae feeding on the menD mutant. The plates were made by using the pathogen grown overnight in TSB medium. Bacteria were peleted and resuspended in semi-solid agar containing 0.9% sodium chloride without bovine serum (Column A) and seven-fold diluted bovine serum (column B). Each set of the plates was supplemented with either soft agar (left) or SM2 medium (right). Plates were incubated at room temperature and data was recorded after 48 hours (Clearing). Plates were photographed using a camera attached to a Olympus microscope at 8× magnification. Clearing zone shows feeding front of amoebae and structures inside are showing aggregation, slugs and mature fruiting bodies of amoebae with spores. Photos in a column marked as ("non nutrient agar") were taken without a light diffuser in the microscope. Therefore, contrast between clearing zones and confluent bacterial growth is enhanced in comparison to the two panels in the column A (absence of serum).

Figure 13:
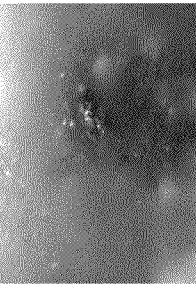
FIG. 13 shows feeding of amoebae on Wide Type *Staphylococcus* in presence or absence of serum.
Figure 13:
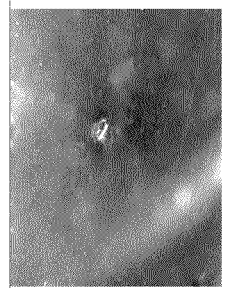
Figure 13:
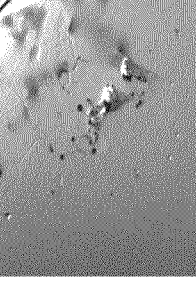
Figure 13:
Figure 13:
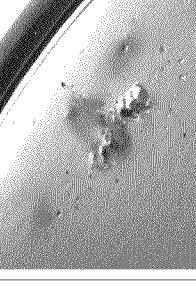
Figure 13:
Figure 13:
Figure 13:
Figure 13:
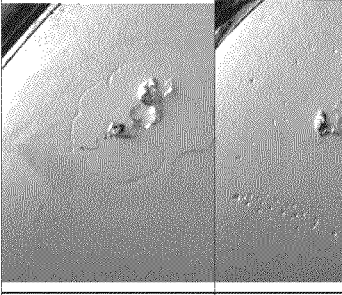
Figure 13:
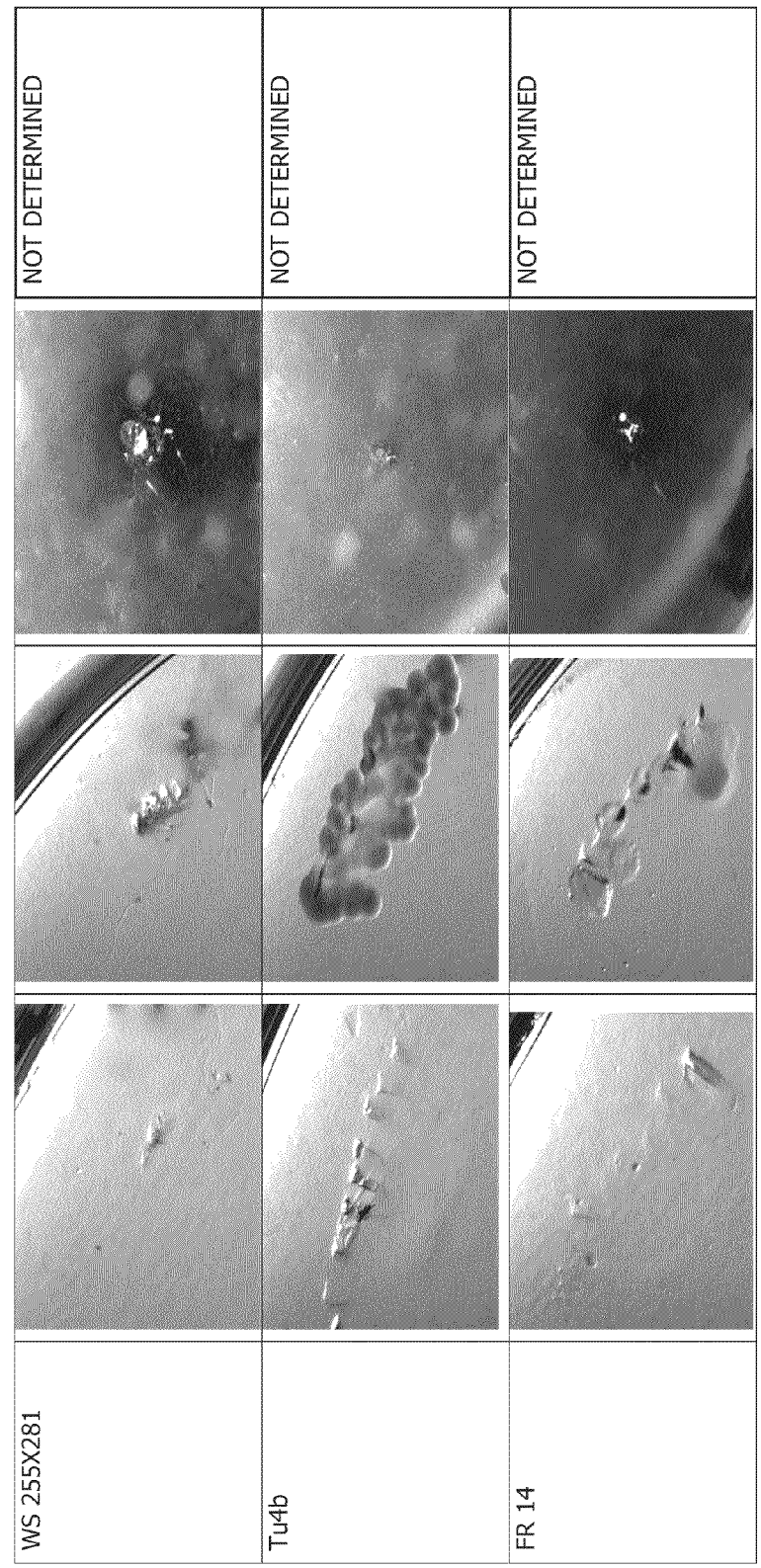

FIG. 13 shows feeding of amoebae on Wide Type *Staphylococcus* in the presence or absence of serum. Shown are pictures of amoebae feeding on the mend+ strain of *S. aureus*. The plates were made by using the pathogen grown overnight in TSB medium. Bacteria were peleted and resuspended in semi-solid agar containing 0.9% sodium chloride without bovine serum (Column A) and seven-fold diluted bovine serum (column B). Each set of the plates was supplemented with either soft agar (left) or SM2 medium (right). Plates were incubated at room temperature and data was recorded after 48 hours (Clearing). Plates were photographed using a camera attached to an Olympus microscope at 8× magnification. Clearing zone shows feeding front of amoebae and structures inside are showing aggregation, slugs and mature fruiting bodies of amoebae with spores. Photos in a column marked as ("non nutrient agar") were taken without a light diffuser in the microscope. Therefore, contrast between clearing zones and confluent bacterial growth is enhanced in comparison to the two panels in the column A (absence of serum).

Feeding was not affected or minimally effected by serum with the following amoebae: WS321.7, WS255×281, Fr14.

Modest inhibition by serum was observed with the following amoebae Turkey 27, WS57.7, WS371A, X3 WS309. Poor or no growth was observed with the Salvador strain of amebae.

Example 6

Agricultural Applications

Figure 8:
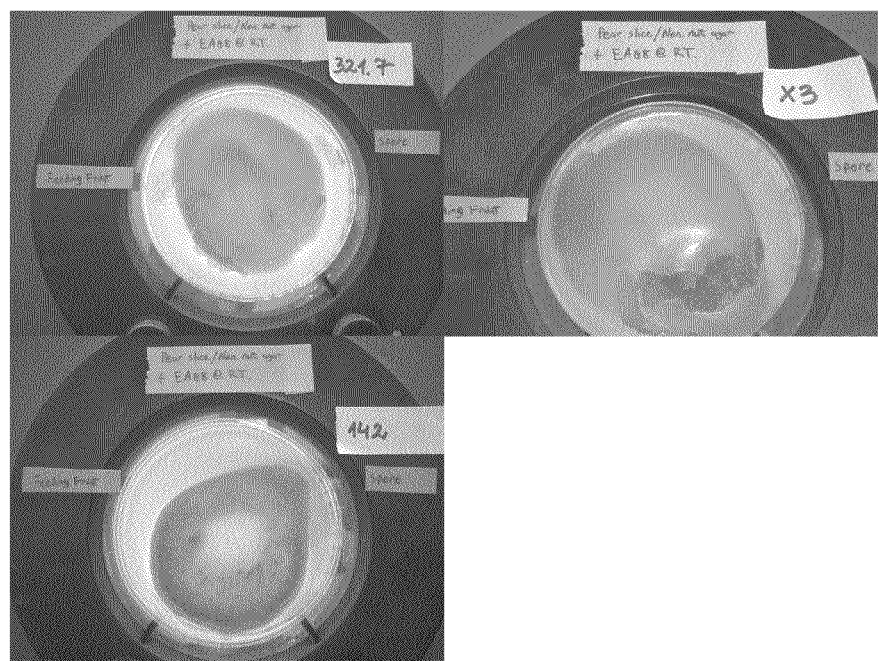
FIG. 8 shows feeding of amoebae on *Erwinia amylovora* grown in SM2 medium "impregnated" with a slice of a pear. As indicated the plate surface was inoculated either with spores or with amoebae. Two amoebae isolates were tested, X3 and WS 321.7

This example demonstrates the use of amoebae as antimicrobial agents in agricultural applications. In these methods, the amoebae are applied to plant surfaces (FIG. 8) to reduce or prevent microbial plant disease or spoilage. Results are shown in FIGS. 8 and 14-15.

Figure 14:
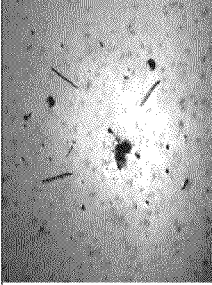
FIG. 14 shows feeding of amoebae on natural isolates of virulent strains of *Erwinia amylovora* (88, 85.1 and A97.1) a causative agent of Fire blight in fruit crops.
Figure 14:
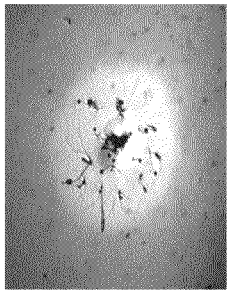
Figure 14:
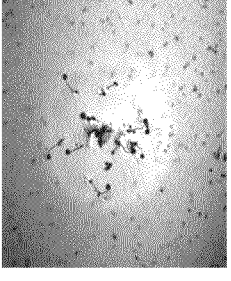
Figure 14:
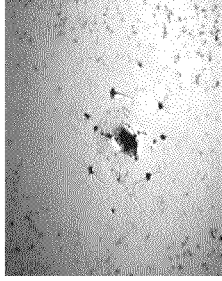
Figure 14:
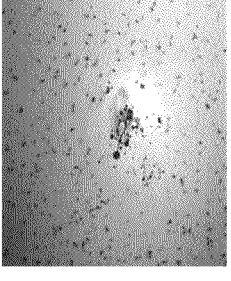
Figure 14:
Figure 14:
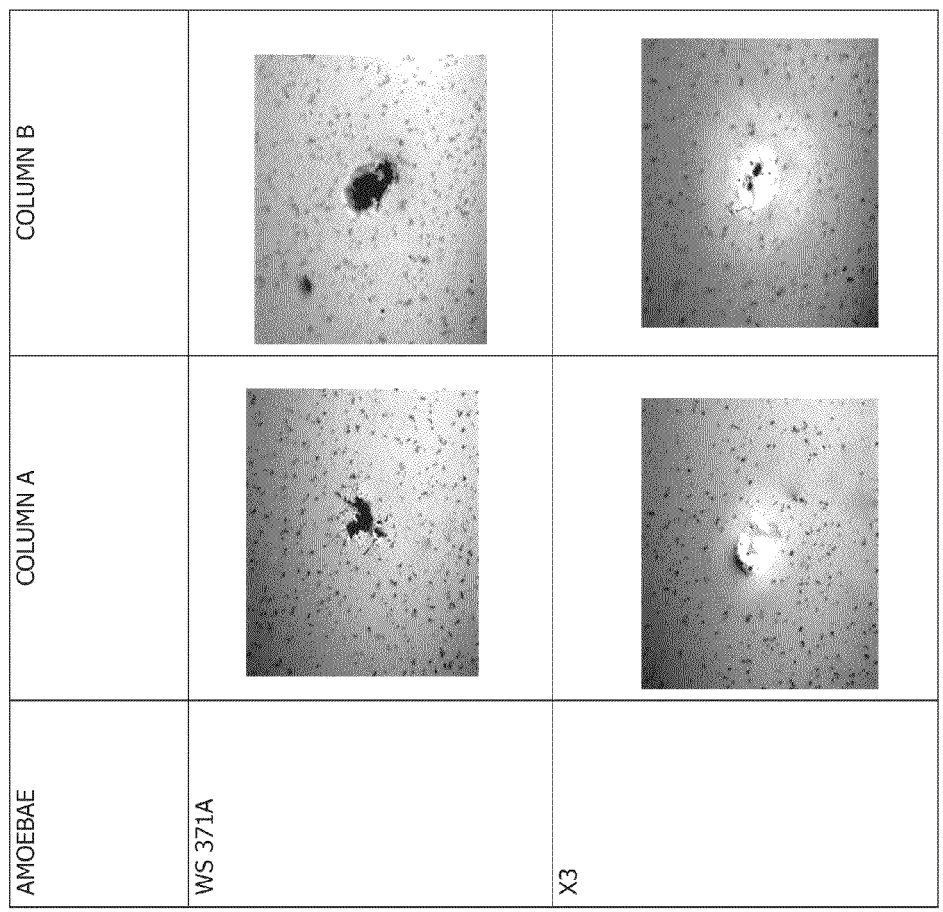
Figure 14:
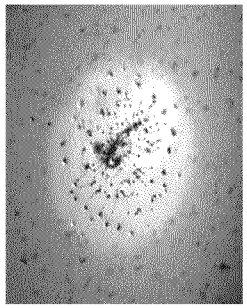
Figure 14:
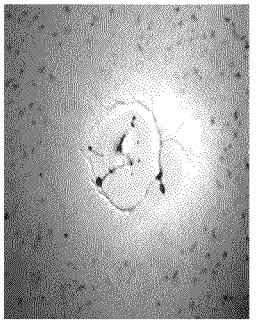
Figure 14:
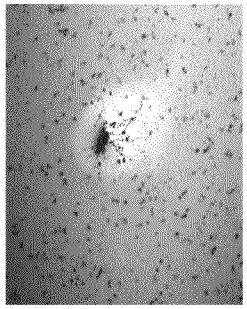
Figure 14:
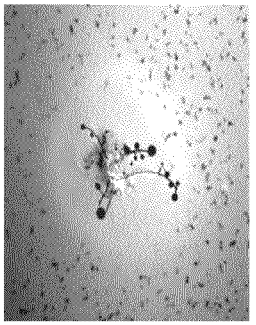
Figure 14:
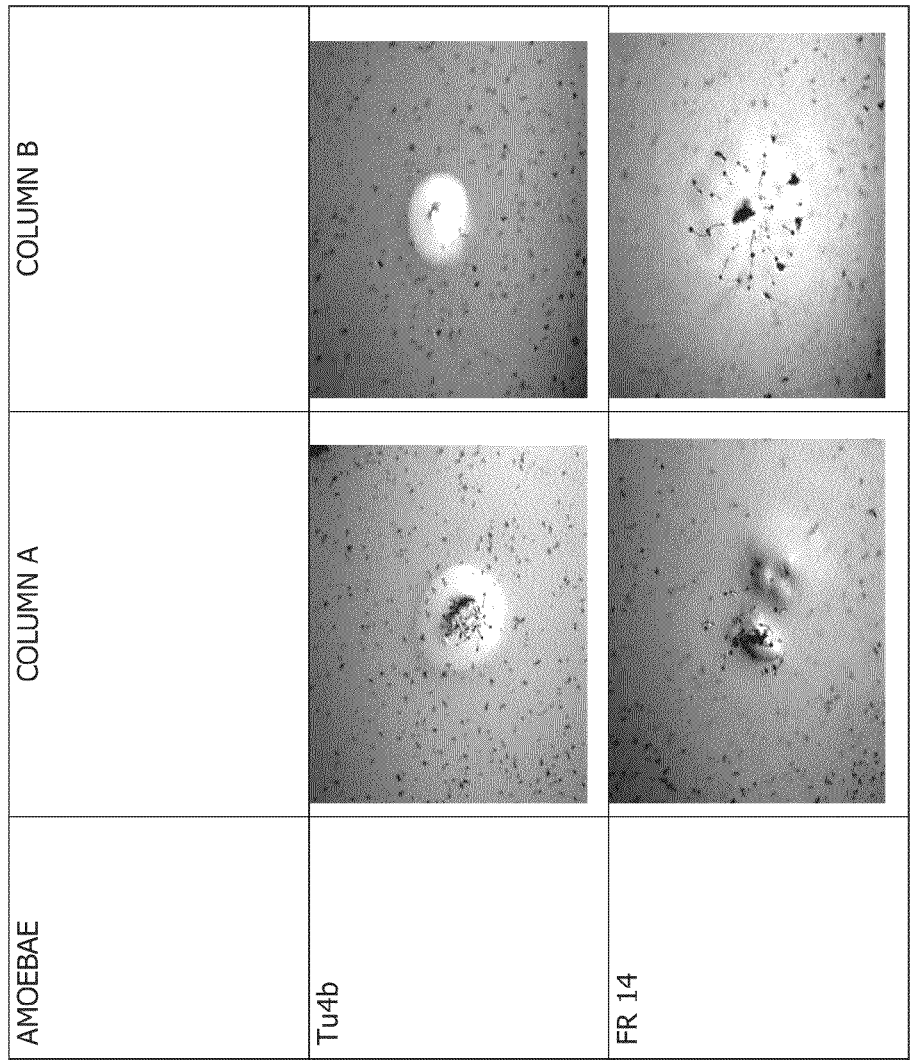
Figure 14:
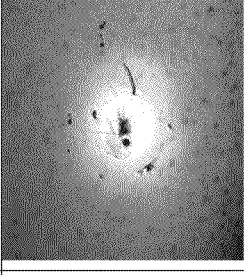
Figure 14:
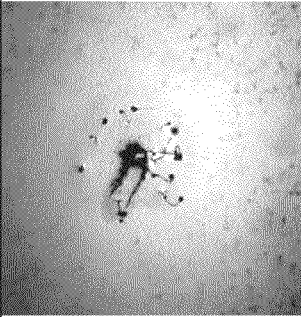
Figure 14:
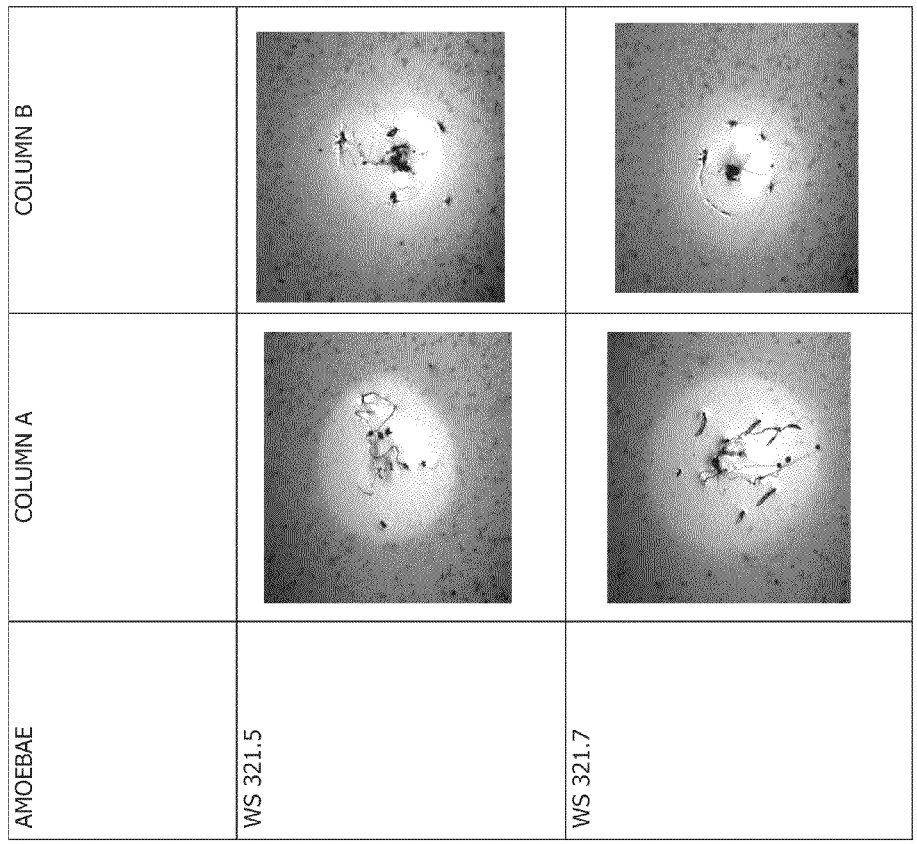
Figure 14:
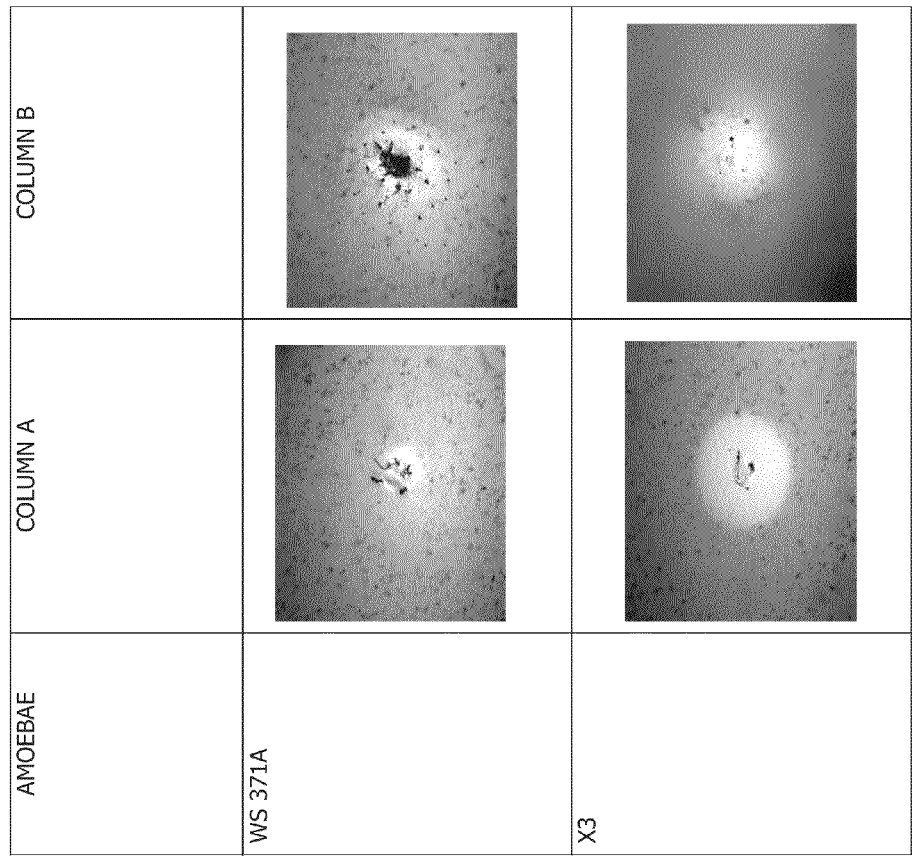
Figure 14:
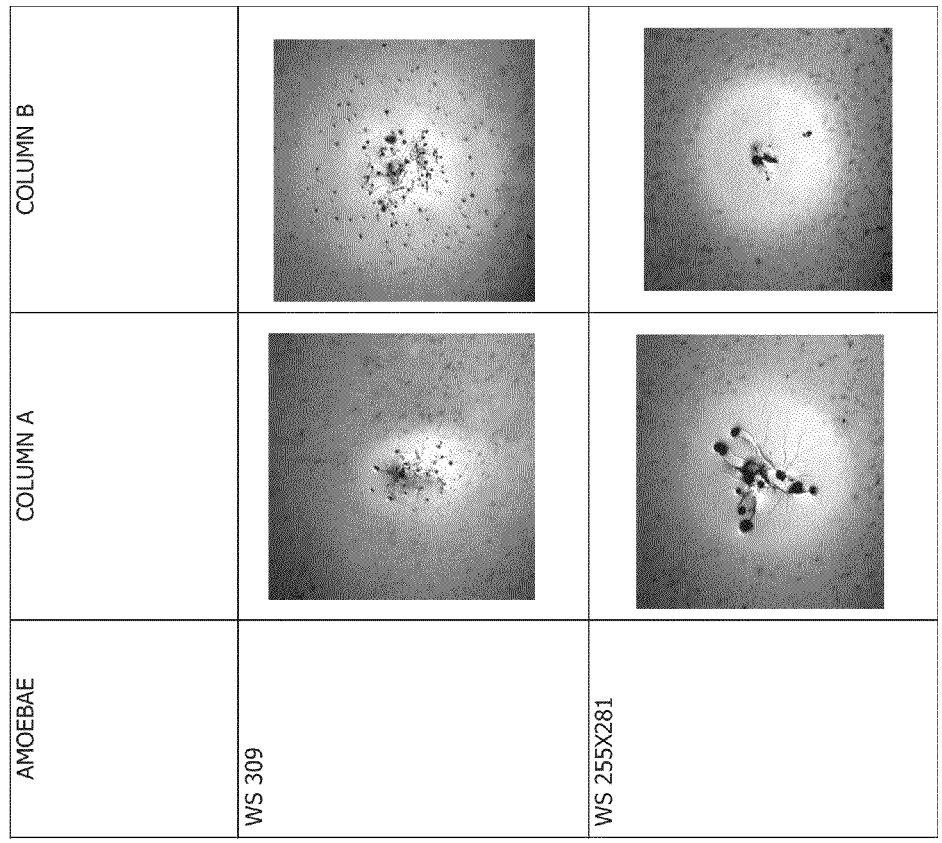
Figure 14:
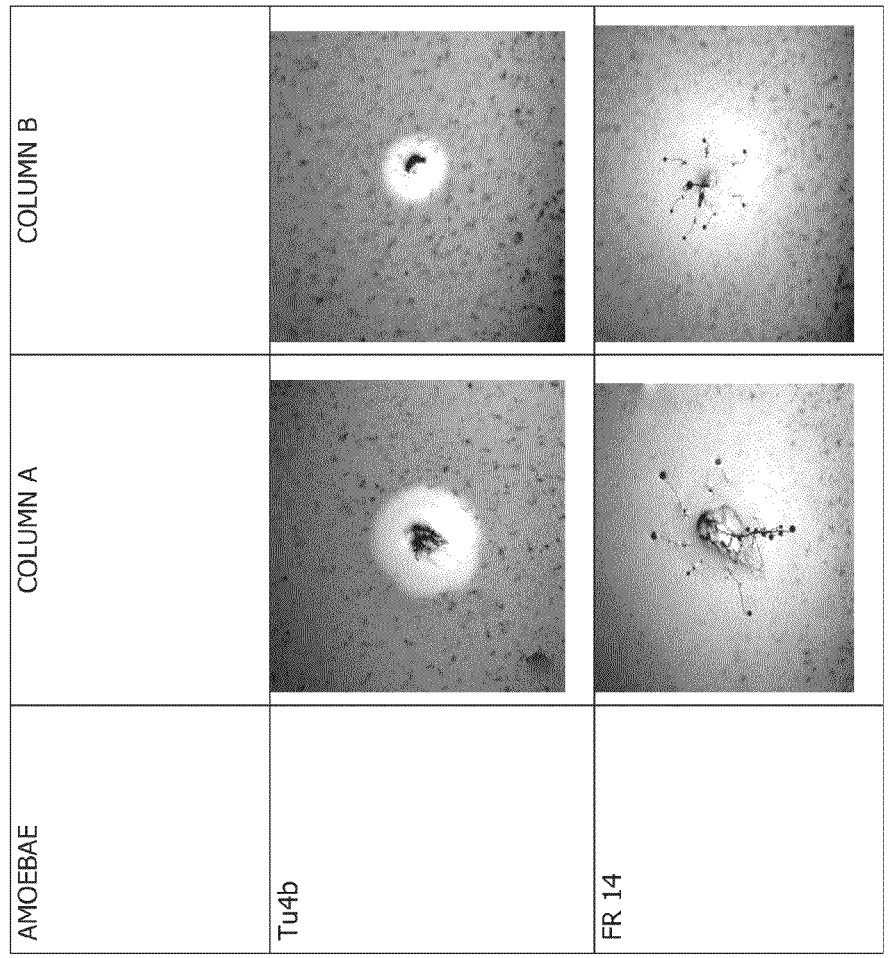
Figure 14:
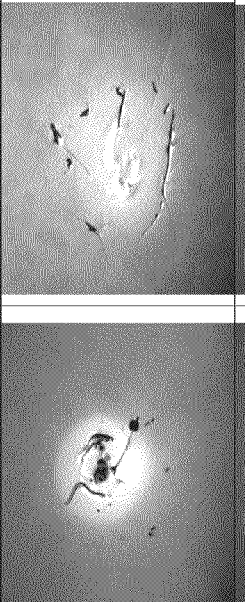
Figure 14:
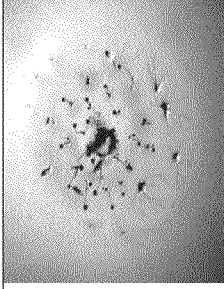
Figure 14:
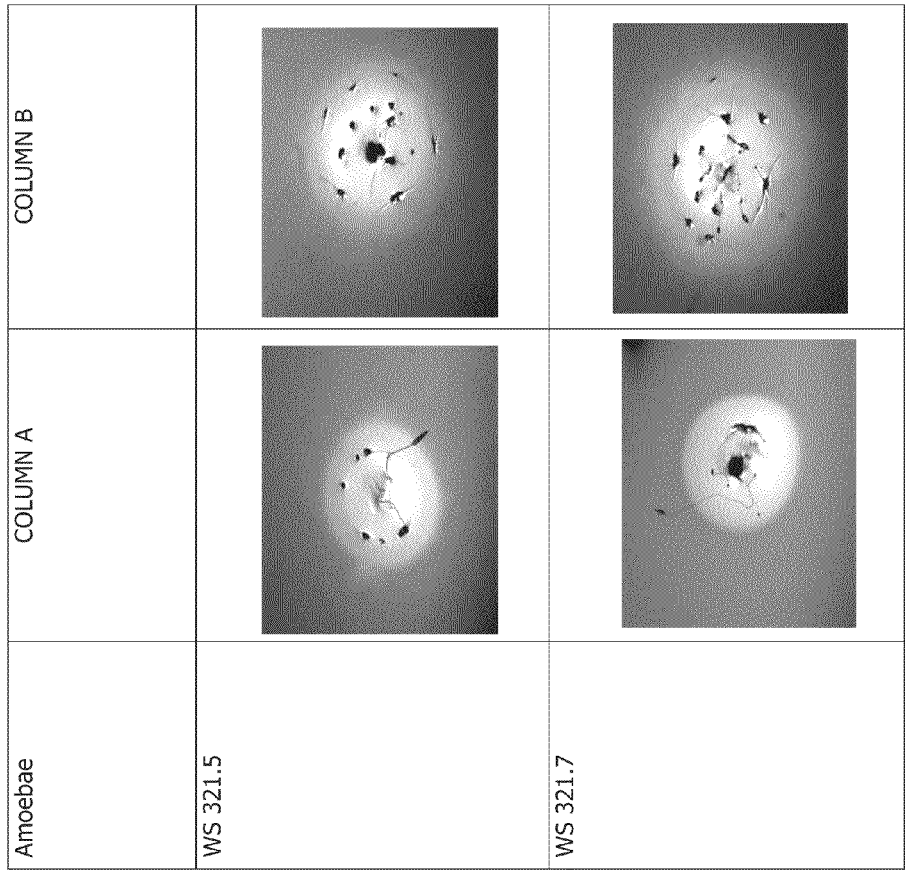
Figure 14:
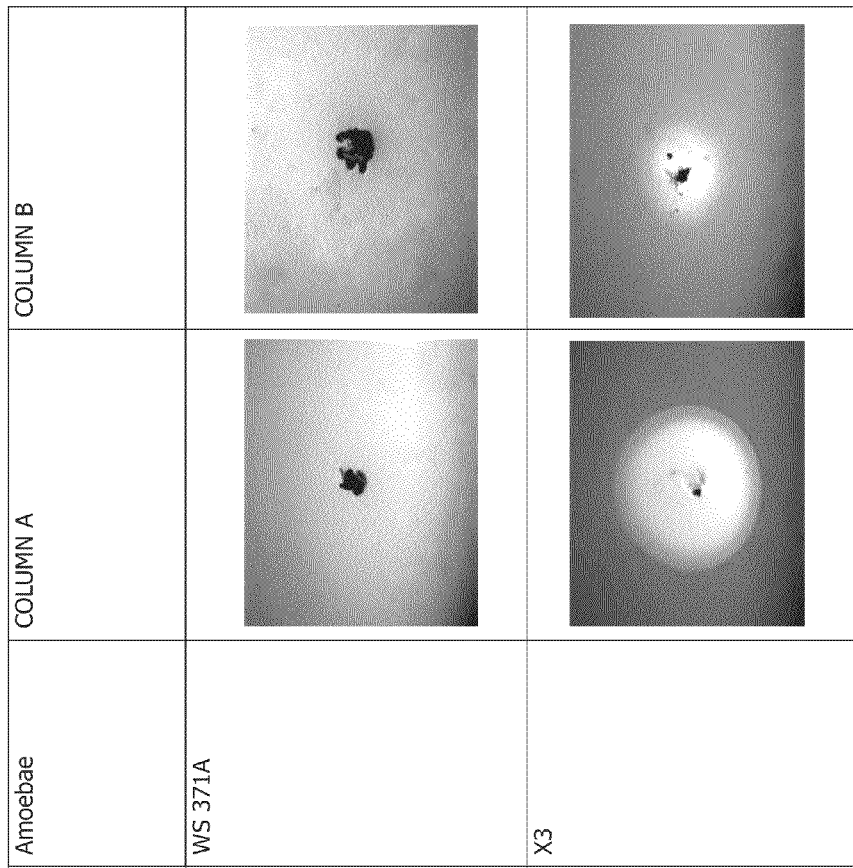
Figure 14:
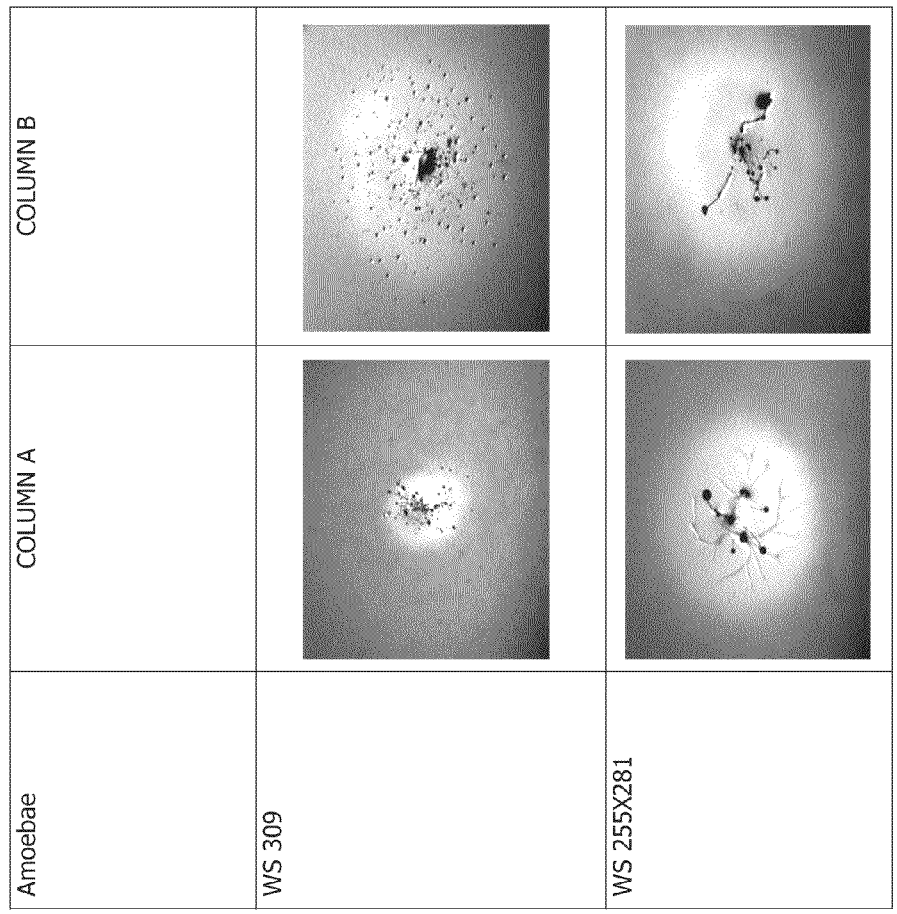
Figure 14:
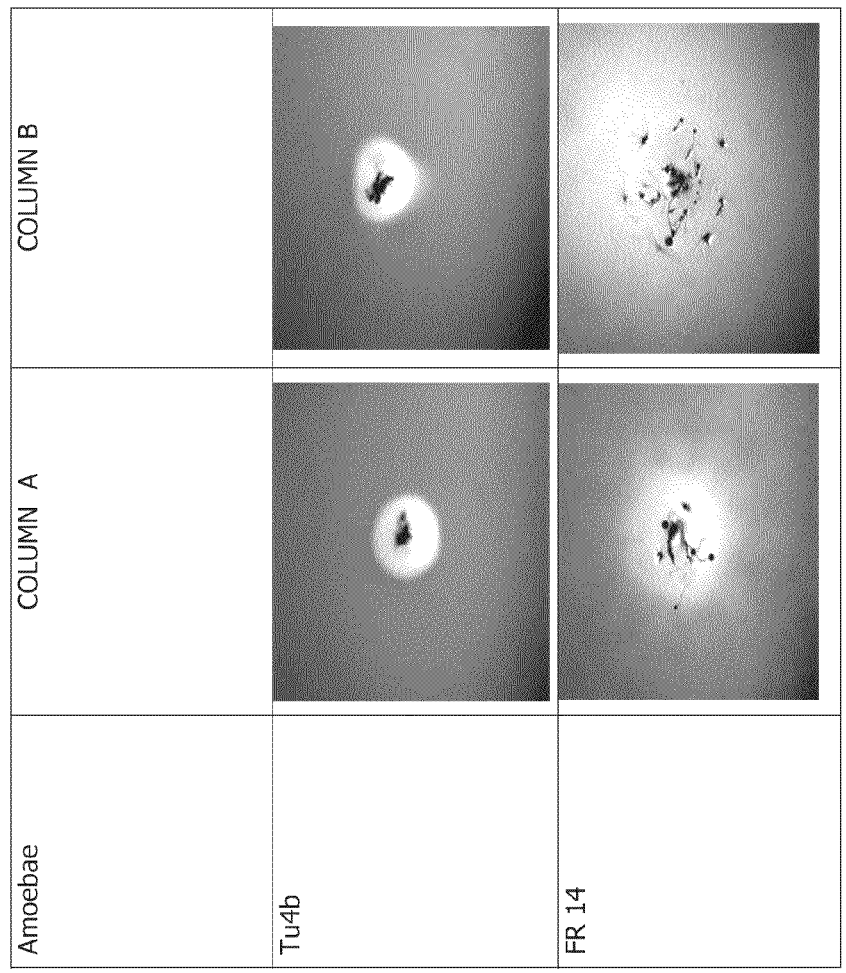
Figure 15:
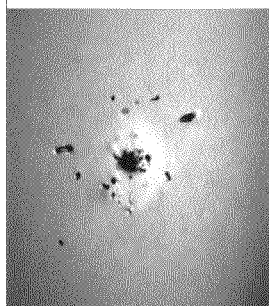
FIG. 15 shows feeding of amoebae on natural isolate virulent agent of bean disease *Pseudomonas* syringe 207.2.
Figure 15:
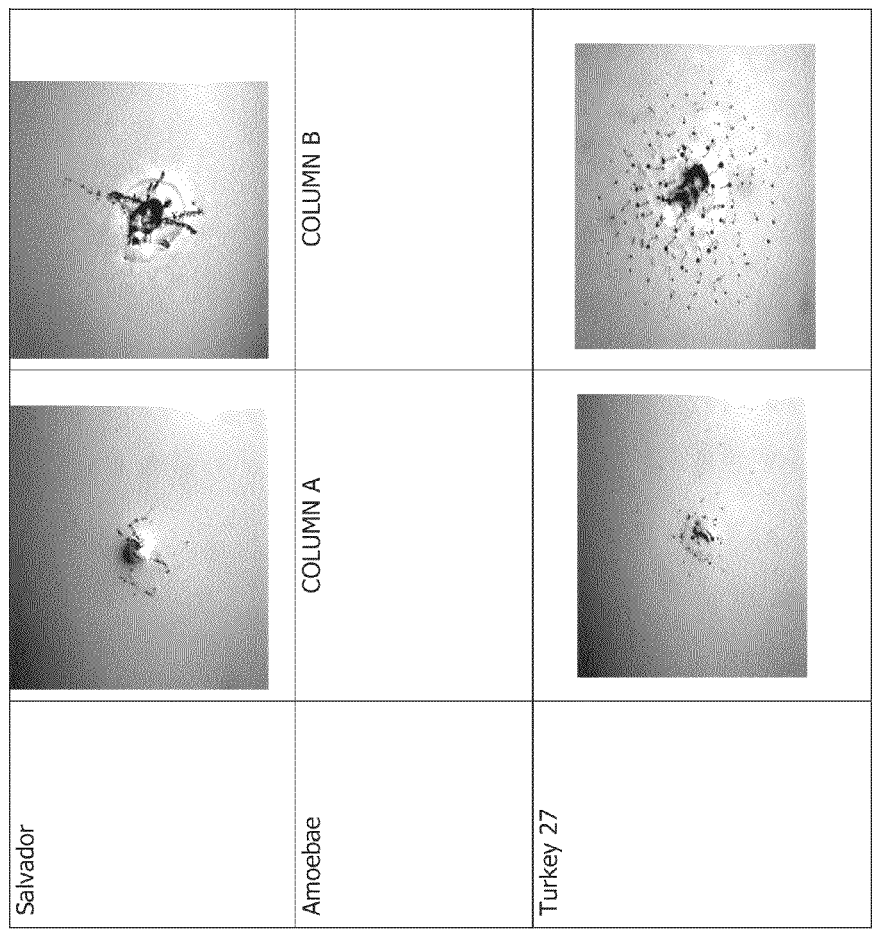

FIG. 14 shows feeding of amoebae on natural isolates of virulent strains of *Erwinia amylovora* (88, 85.1 and A97.1) a causative agent of Fire blight in fruit crops. Column A presents feeding and development of amoebae in the presence of *Erwinia amylovora* virulent isolates. Overnight culture of bacteria grown in SM2 medium was pelleted and resuspended in 0.9% sodium chloride for non-nutrient conditions and in SM2 liquid media for nutrient conditions (Column B). White irregular zone represents feeding front of free living amoebae digesting bacteria inside this zone aggregation, slugs and well developed fruiting bodies with spores are visible as well. Pictures were taken using Olympus microscope/camera at 7-fold magnification.

FIG. 15 shows feeding of amoebae on natural isolate virulent agent of bean disease *Pseudomonas* syringe 207.2. Column A shows zones of growth (or lack thereof) of amoebae on plates inoculated with *P. syringiae* 207.2. The plates were prepared by using the pathogen grown overnight in SM2 medium. Bacteria were peleted and resuspended in semi-solid agar containing MS2 nutrient agar (column A) or non nutrient agar (Column B). Plates were incubated at room temperature and data was recorded after 48 hours (Clearing). Plates were photographed using a camera attached to an Olympus microscope at 8× magnification. Clearing zone shows feeding front of amoebae and structures inside are showing aggregation, slugs and mature fruiting bodies of amoebae with spores.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A system, comprising:

a) a composition comprising one or more species of amoebae of the phylum Mycetozoa; and b) a medical device comprising said composition.

2. The system of claim 1, wherein said medical device is selected from the group consisting of a medical implant, a wound care device, a drug delivery device, a birth control device, and body cavity and personal protection device.

3. The system of claim 2, wherein said medical implant is selected from the group consisting of a urinary catheter, an intravascular catheter, a dialysis shunt, a wound drain tube, a skin suture, a vascular graft, an implantable mesh, an intraocular device, and a heart valve.

4. The system of claim 2, wherein said wound care device is selected from the group consisting of a general wound dressing, a biologic graft material, a tape closure or dressing, and a surgical incision drape.

5. The system of claim 2, wherein said delivery device is selected from the group consisting of needles, drug delivery skin patches, drug delivery mucosal patches and medical sponges.

6. The system of claim 2, wherein said body cavity and personal protection device is selected from the group consisting of tampons, sponges, surgical and examination gloves, and toothbrushes.

7. The system of claim 2, wherein said birth control device is selected from the group consisting of intrauterine devices (IUDs), diaphragms, and condoms.

8. The system of claim 1, wherein said composition comprises two or more species of amoebae.

9. The system of claim 1, wherein said amoebae are selected from the group consisting of *Polyspondillum pallidum* Salvador, *Polysphondylium violaceum* WS-371a, *Dictyostelium discoideum* WS 647, *Dictyostelium mucoroides* WS 142, *Dictyostelium mucoroides* Turkey 27, *Actyostilium leptosomum* WS 57.5, *Dictyostelium purpureum* WS 321.5, *Dictyostelium purpureum* WS 321.7, *Dictyostelium discoideum* X3, *Dictyostelium mucoroides* WS309, *Dictyostelium mucoroides* WS 255×281, *Dictyostelium lavandullum* Tu4b and *Polispondillum candidum* Fr14.

10. The system of claim 1, wherein said composition further comprises a non-amoebae anti-microbial agent.

11. The system of claim 1, wherein said composition is a pharmaceutical composition.

12. A kit, comprising:

a) a composition comprising one or more species of amoebae of the phylum Mycetozoa; and b) a medical device.

13. The kit of claim 12, wherein said composition is on or in said medical device.

14. The kit of claim 12, wherein said medical device is selected from the group consisting of a medical implant, a wound care device, a drug delivery device, a birth control device, and body cavity and personal protection device.

15. The kit of claim 14, wherein said medical implant is selected from the group consisting of a urinary catheter, an intravascular catheter, a dialysis shunt, a wound drain tube, a skin suture, a vascular graft, an implantable mesh, an intraocular device, and a heart valve.

16. The kit of claim 14, wherein said wound care device is selected from the group consisting of a general wound dressing, a biologic graft material, a tape closure or dressing, and a surgical incision drape.

17. The kit of claim 14, wherein said delivery device is selected from the group consisting of needles, drug delivery skin patches, drug delivery mucosal patches and medical sponges.

18. The kit of claim 14, wherein said body cavity and personal protection device is selected from the group consisting of tampons, sponges, surgical and examination gloves, and toothbrushes.

19. The kit of claim 14, wherein said birth control device is selected from the group consisting of intrauterine devices (IUDs), diaphragms, and condoms.

20. The kit of claim 12, wherein said composition comprises two or more species of amoebae.

21. The kit of claim 12, wherein said amoebae are selected from the group consisting of *Polyspondillum pallidum* Salvador, *Polysphondylium violaceum* WS-371a, *Dictyostelium discoideum* WS 647, *Dictyostelium mucoroides* WS 142,

*Dictyostelium mucoroides* Turkey 27, *Actyostilium leptosomum* WS 57.5, *Dictyostelium purpureum* WS 321.5, *Dictyostelium purpureum* WS 321.7, *Dictyostelium discoideum* X3, *Dictyostelium mucoroides* WS309, *Dictyostelium mucoroides* WS 255×281, *Dictyostelium lavandullum* Tu4b and *Polispondillum candidum* Fr14.

22. The kit of claim 12, wherein said composition further comprises a non-amoebae anti-microbial agent.

* * * * *